US012799173B2

(12) United States Patent
Maglia et al.

(10) Patent No.: US 12,799,173 B2
(45) **Date of Patent: *Nov. 17, 2026**

(54) BIOLOGICAL NANOPORES FOR BIOPOLYMER SENSING AND SEQUENCING BASED ON FRAC ACTINOPORIN

(71) Applicant: Rijksuniversiteit Groningen, Groningen (NL)

(72) Inventors: Giovanni Maglia, Glimmen (NL); Carsten Wloka, Hohen Neuendorf (DE); Natalie Lisa Mutter, Groningen (NL); Misha Soskine, Paris (FR); Gang Huang, Groningen (NL)

(73) Assignee: Rijksuniversiteit Groningen, Groningen (NL)

( * ) Notice: Subject to any disclaimer, the term of this patent is extended or adjusted under 35 U.S.C. 154(b) by 971 days.

This patent is subject to a terminal disclaimer.

(21) Appl. No.: 17/696,949

(22) Filed: Mar. 17, 2022

(65) Prior Publication Data

US 2022/0242922 A1 Aug. 4, 2022

Related U.S. Application Data

(63) Continuation of application No. 16/317,119, filed as application No. PCT/NL2017/050331 on May 24, 2017, now Pat. No. 11,312,755.

(60) Provisional application No. 62/360,999, filed on Jul. 12, 2016.

(51) Int. Cl.

| | |
|---|---|
| ***C07K 14/00*** | (2006.01) |
| ***C07K 14/435*** | (2006.01) |
| ***C12Q 1/6869*** | (2018.01) |
| ***G01N 27/447*** | (2006.01) |
| ***G01N 33/487*** | (2006.01) |
| *B82Y 5/00* | (2011.01) |

(52) U.S. Cl.

CPC ...... *C07K 14/43595* (2013.01); *C12Q 1/6869* (2013.01); *G01N 27/44791* (2013.01); *G01N 33/48721* (2013.01); *B82Y 5/00* (2013.01); *C07K 2319/00* (2013.01); *C07K 2319/03* (2013.01); *C07K 2319/21* (2013.01); *C07K 2319/22* (2013.01)

(58) Field of Classification Search

CPC .......... C07K 14/43595; C07K 2319/00; C07K 2319/03; C07K 2319/21; C07K 2319/22; C12Q 1/6869; G01N 27/44791; G01N 33/48721; B82Y 5/00

See application file for complete search history.

(56) References Cited

U.S. PATENT DOCUMENTS

| | | | |
|---|---|---|---|
| 5,795,782 | A | 8/1998 | Church et al. |
| 6,015,714 | A | 1/2000 | Baldarelli et al. |
| 6,267,872 | B1 | 7/2001 | Akeson et al. |
| 6,362,001 | B1 | 3/2002 | Cai et al. |
| 6,362,002 | B1 | 3/2002 | Denison et al. |
| 6,428,959 | B1 | 8/2002 | Deamer |
| 6,464,842 | B1 | 10/2002 | Golovchenko et al. |
| 6,465,946 | B1 | 10/2002 | Yoon et al. |
| 6,617,113 | B2 | 9/2003 | Deamer |
| 6,627,067 | B1 | 9/2003 | Branton et al. |
| 6,673,615 | B2 | 1/2004 | Denison et al. |
| 6,746,594 | B2 | 6/2004 | Akeson et al. |
| 7,238,485 | B2 | 7/2007 | Akeson et al. |
| 7,622,934 | B2 | 11/2009 | Hibbs et al. |
| 7,635,572 | B2 | 12/2009 | Zhou et al. |
| 7,867,716 | B2 | 1/2011 | Kang et al. |
| 7,968,702 | B2 | 6/2011 | Wegener et al. |
| 8,324,914 | B2 | 12/2012 | Chen et al. |
| 8,377,643 | B2 | 2/2013 | Mehra et al. |
| 8,500,982 | B2 | 8/2013 | Akeson et al. |
| 8,581,605 | B2 | 11/2013 | White et al. |
| 8,673,550 | B2 | 3/2014 | Gundlach et al. |
| 8,961,763 | B2 | 2/2015 | Dunbar et al. |
| 8,986,928 | B2 | 3/2015 | Turner et al. |
| 9,017,937 | B1 | 4/2015 | Turner et al. |
| 9,052,275 | B2 | 6/2015 | Khattak et al. |
| 9,121,064 | B2 | 9/2015 | Turner et al. |
| 9,127,313 | B2 | 9/2015 | Brown et al. |
| 9,377,437 | B2 | 6/2016 | Chen et al. |
| 9,494,554 | B2 | 11/2016 | Davis et al. |

(Continued)

FOREIGN PATENT DOCUMENTS

| | | |
|---|---|---|
| CN | 104710519 A | 6/2015 |
| CN | 112480204 A | 3/2021 |

(Continued)

OTHER PUBLICATIONS

Nature Communications published Feb. 26, 2015. (Year: 2015).*

(Continued)

*Primary Examiner* — Catherine S Hibbert

(74) *Attorney, Agent, or Firm* — Wilson Sonsini Goodrich & Rosati

(57) ABSTRACT

The invention relates generally to the field of nanopores and the use thereof in various applications, such as analysis of biopolymers and macromolecules, typically by making electrical measurements during translocation through a nanopores. Provided is a system comprising a funnel-shaped proteinaceous nanopore comprising an α-helical pore-forming toxin that is a member from the actinoporin protein family, more in particular Fragaceatoxin C (FraC), a mutant FraC, a FraC paralog, or a FraC homolog.

17 Claims, 12 Drawing Sheets

Figure 1:
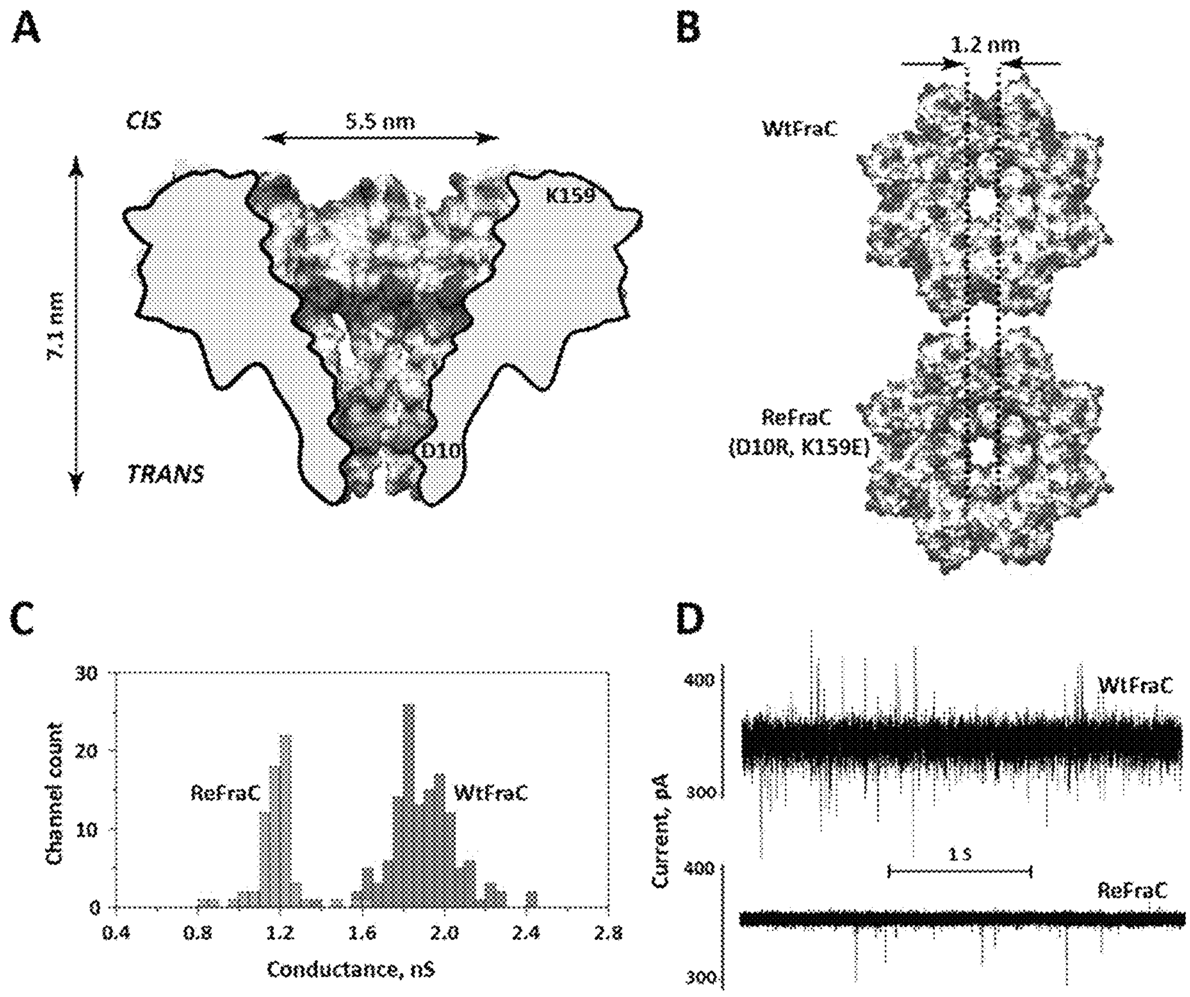

(12 of 12 Drawing Sheet(s) Filed in Color)

Specification includes a Sequence Listing.

(56) References Cited

U.S. PATENT DOCUMENTS

| | | | |
|---|---|---|---|
| 9,534,024 | B2 | 1/2017 | Gundlach et al. |
| 9,562,874 | B2 | 2/2017 | Martin et al. |
| 9,724,691 | B2 | 8/2017 | Khattak et al. |
| 9,766,248 | B2 | 9/2017 | Lindsay et al. |
| 9,863,912 | B2 | 1/2018 | Dunbar et al. |
| 9,868,987 | B2 | 1/2018 | Turner |
| 9,903,820 | B2 | 2/2018 | Meller et al. |
| 9,983,191 | B2 | 5/2018 | Morin |
| 10,036,064 | B2 | 7/2018 | Merriman et al. |
| 10,036,739 | B2 | 7/2018 | Hovis et al. |
| 10,195,606 | B2 | 2/2019 | Khattak et al. |
| 10,209,217 | B2 | 2/2019 | Gentalen |
| 10,215,768 | B2 | 2/2019 | Sanghera et al. |
| 10,221,450 | B2 | 3/2019 | Heron et al. |
| 10,345,240 | B2 | 7/2019 | Chan et al. |
| 10,364,462 | B2 | 7/2019 | Stava et al. |
| 10,458,978 | B2 | 10/2019 | Cary |
| 10,514,380 | B2 | 12/2019 | Takulapalli |
| 10,612,083 | B2 | 4/2020 | Gundlach et al. |
| 10,656,117 | B2 | 5/2020 | Mayer et al. |
| 10,712,254 | B2 | 7/2020 | Bayley et al. |
| 10,787,705 | B2 | 9/2020 | Esfandyarpour et al. |
| 10,794,895 | B2 | 10/2020 | Xie |
| 10,870,883 | B2 | 12/2020 | Gundlach et al. |
| 10,883,140 | B2 | 1/2021 | Church et al. |
| 10,900,067 | B2 | 1/2021 | Aksimentiev et al. |
| 10,961,576 | B2 | 3/2021 | Boyanov et al. |
| 10,976,311 | B2 | 4/2021 | Maglia et al. |
| 10,996,219 | B2 | 5/2021 | Chee |
| 11,002,657 | B2 | 5/2021 | Pelta et al. |
| 11,034,734 | B2 | 6/2021 | Howorka et al. |
| 11,061,013 | B2 | 7/2021 | Mir |
| 11,150,216 | B2 | 10/2021 | Chen et al. |
| 11,162,935 | B2 | 11/2021 | Wang et al. |
| 11,261,488 | B2 | 3/2022 | Craig et al. |
| 11,282,585 | B2 | 3/2022 | Patel et al. |
| 11,312,755 | B2 | 4/2022 | Maglia et al. |
| 11,313,857 | B2 | 4/2022 | Wanunu et al. |
| 11,339,365 | B2 | 5/2022 | Nivala et al. |
| 11,391,693 | B2 | 7/2022 | Boyanov et al. |
| 11,618,897 | B2 | 4/2023 | Kim et al. |
| 11,644,437 | B2 | 5/2023 | Xie et al. |
| 11,703,476 | B2 | 7/2023 | Wanunu et al. |
| 11,821,903 | B2 | 11/2023 | Woolfson et al. |
| 11,840,556 | B2 | 12/2023 | Jayasinghe et al. |
| 11,845,779 | B2 | 12/2023 | Dal Peraro et al. |
| 12,105,079 | B2 | 10/2024 | Huang et al. |
| 12,235,260 | B2 | 2/2025 | Maglia et al. |
| 2003/0104428 | A1 | 6/2003 | Branton et al. |
| 2004/0121525 | A1 | 6/2004 | Chopra et al. |
| 2008/0287656 | A1 | 11/2008 | Peters et al. |
| 2010/0297638 | A1 | 11/2010 | Bayley et al. |
| 2011/0174625 | A1 | 7/2011 | Akeson et al. |
| 2011/0193249 | A1 | 8/2011 | Chen et al. |
| 2011/0249259 | A1 | 10/2011 | Van Dorpe et al. |
| 2011/0311965 | A1 | 12/2011 | Maglia et al. |
| 2012/0055792 | A1 | 3/2012 | Gundlach et al. |
| 2012/0107802 | A1 | 5/2012 | Stoddart et al. |
| 2013/0017538 | A1 | 1/2013 | Ionescu-Zanetti et al. |
| 2013/0161194 | A1 | 6/2013 | Jeon et al. |
| 2014/0106472 | A1 | 4/2014 | Ervin et al. |
| 2014/0255921 | A1 | 9/2014 | Moysey et al. |
| 2014/0335527 | A1 | 11/2014 | Goel |
| 2015/0031020 | A1 | 1/2015 | Jayasinghe et al. |
| 2015/0191709 | A1 | 7/2015 | Heron et al. |
| 2016/0018384 | A1 | 1/2016 | Lindsay et al. |
| 2016/0032235 | A1 | 2/2016 | Segard |
| 2016/0032236 | A1 | 2/2016 | Nivala et al. |
| 2016/0169864 | A1 | 6/2016 | Grinstaff et al. |
| 2016/0273032 | A1 | 9/2016 | Esfandyarpour et al. |
| 2017/0315109 | A1 | 11/2017 | Alden et al. |
| 2018/0364214 | A1 | 12/2018 | Maglia et al. |
| 2019/0071721 | A1 | 3/2019 | Jayasinghe et al. |
| 2019/0128867 | A1 | 5/2019 | Movileanu et al. |
| 2019/0227028 | A1 | 7/2019 | Patolsky et al. |
| 2020/0123594 | A1 | 4/2020 | Rothberg et al. |
| 2020/0348307 | A1 | 11/2020 | Beierle et al. |
| 2021/0033591 | A1 | 2/2021 | Ambroso et al. |
| 2021/0088511 | A1 | 3/2021 | Crisalli et al. |
| 2021/0189482 | A1 | 6/2021 | Akeson et al. |
| 2021/0255075 | A1 | 8/2021 | Ren et al. |
| 2021/0308677 | A1 | 10/2021 | Goel |
| 2021/0325365 | A1 | 10/2021 | Huang et al. |
| 2021/0340192 | A1 | 11/2021 | Nivala |
| 2021/0363577 | A1 | 11/2021 | Clarke et al. |
| 2021/0372959 | A1 | 12/2021 | Liu et al. |
| 2022/0091093 | A1 | 3/2022 | Wanunu et al. |
| 2022/0162568 | A1 | 5/2022 | Haque et al. |
| 2022/0226820 | A1 | 7/2022 | Khurana et al. |
| 2022/0277814 | A1 | 9/2022 | Nivala |
| 2022/0283140 | A1 | 9/2022 | Wanunu et al. |
| 2022/0299469 | A1 | 9/2022 | Boyanov et al. |
| 2022/0396758 | A1 | 12/2022 | Nivala et al. |
| 2022/0412948 | A1 | 12/2022 | Maglia et al. |
| 2023/0024319 | A1 | 1/2023 | Heron et al. |
| 2023/0048421 | A1 | 2/2023 | Zhang et al. |
| 2023/0090454 | A1 | 3/2023 | Kapp et al. |
| 2023/0194499 | A1 | 6/2023 | Zou et al. |
| 2023/0220002 | A1 | 7/2023 | Long et al. |
| 2023/0221296 | A1 | 7/2023 | Long et al. |
| 2024/0002925 | A1 | 1/2024 | Anslyn et al. |
| 2024/0003909 | A1 | 1/2024 | Li |
| 2024/0159768 | A1 | 5/2024 | Lucas et al. |
| 2024/0201165 | A1 | 6/2024 | Maglia et al. |
| 2024/0288416 | A1 | 8/2024 | Maglia et al. |
| 2026/0002925 | A1 | 1/2026 | Rijksuniversiteit |

FOREIGN PATENT DOCUMENTS

| | | | |
|---|---|---|---|
| CN | 112500459 | A | 3/2021 |
| EP | 1956367 | A1 | 8/2008 |
| EP | 2350122 | A1 | 8/2011 |
| EP | 2814939 | A2 | 12/2014 |
| EP | 2978773 | A1 | 2/2016 |
| EP | 2814939 | B1 | 4/2018 |
| EP | 3485029 | A1 | 5/2019 |
| EP | 3598133 | A1 | 1/2020 |
| EP | 3955002 | A1 | 2/2022 |
| EP | 4070092 | A1 | 10/2022 |
| EP | 4070092 | B1 | 8/2023 |
| EP | 4392437 | A1 | 7/2024 |
| GB | 2431013 | B | 5/2008 |
| JP | 2013540423 | A | 11/2013 |
| NL | 2023062 | B1 | 11/2020 |
| WO | WO-0079257 | A1 | 12/2000 |
| WO | WO-0116328 | A2 | 3/2001 |
| WO | WO-2005124888 | A1 | 12/2005 |
| WO | WO-2006028508 | A2 | 3/2006 |
| WO | WO-2009020682 | A2 | 2/2009 |
| WO | WO-2009044170 | A1 | 4/2009 |
| WO | WO-2010004265 | A1 | 1/2010 |
| WO | 2010/034018 | A2 | 3/2010 |
| WO | WO-2010055307 | A1 | 5/2010 |
| WO | WO-2010082860 | A1 | 7/2010 |
| WO | WO-2010117470 | A2 | 10/2010 |
| WO | WO-2013014451 | A1 | 1/2013 |
| WO | WO-2013123379 | A2 | 8/2013 |
| WO | WO-2014153625 | A1 | 10/2014 |
| WO | WO-2014190299 | A2 | 11/2014 |
| WO | WO-2015040423 | A1 | 3/2015 |
| WO | WO-2015081178 | A1 | 6/2015 |
| WO | WO-2016166232 | A1 | 10/2016 |
| WO | WO-2018012963 | A1 | 1/2018 |
| WO | WO-2020055246 | A1 | 3/2020 |
| WO | WO-2020152563 | A1 | 7/2020 |
| WO | WO-2020160559 | A1 | 8/2020 |
| WO | WO-2021021592 | A1 | 2/2021 |
| WO | WO-2021101378 | A1 | 5/2021 |
| WO | WO-2021111125 | A1 | 6/2021 |
| WO | WO-2022020461 | A1 | 1/2022 |
| WO | WO-2022150659 | A1 | 7/2022 |
| WO | WO-2022245209 | A2 | 11/2022 |
| WO | WO-2023055246 | A1 | 4/2023 |
| WO | WO-2023102502 | A2 | 6/2023 |

(56) References Cited

FOREIGN PATENT DOCUMENTS

| | | | |
|---|---|---|---|
| WO | WO-2023240337 | A1 | 12/2023 |
| WO | WO-2024091123 | A1 | 5/2024 |
| WO | WO-2024091124 | A1 | 5/2024 |

OTHER PUBLICATIONS

Tananka_et_al_Supplemental_Information_2015 (Year: 2015).*
PCT/GB2024/052258 International Search Report and Written Opinion dated Jan. 23, 2025.
U.S. Appl. No. 18/394,833 Office Action dated Dec. 13, 2024.
Vernier, et al. Solubilization and characterization of the anthrax toxin pore in detergent micelles. Protein Science 18:1882-1895 (2009).
PCT/GB2024/052258 Invitation to Pay Additional Fees dated Nov. 27, 2024.
Koji Tanaka et al: Structural basis for self-assembly of a cytolytic pore lined by protein and lipid:, Nature Communications, vol. 6, Feb. 26, 2015 (Feb. 26, 2015), p. 6337, XP055401446, DOI: 10.1038/ncomms7337, p. 337, 2. col. 3. par.
Koldo Morante et al: "A Pore-Forming Toxin Requires a Specific Residue for Its Activity in Membranes with Particular Physicochemical Properties", Journal of Biological Chemistry, vol. 290, No. 17, Apr. 24, 2015 (Apr. 24, 2015), pp. 10850-10861, XP055401448, us ISSN: 0021-9258, DOI: 10.1074/jbc.M114.615211.
Bellomio A et al: "Purification, cloning and characterization of fragaceatoxin C, a novel actinoporin from the sea anemone Actinia fragacea", Toxicon, Elmsford, NY, US, vol. 54, No. 6, Nov. 1, 2009 (Nov. 1, 2009), pp. 869-880, XP026499390, ISSN: 0041-0101, DOI: 10.1016/J.TOXICON.2009.06.022 [retrieved on Jun. 27, 2009].
Afshar Bakshloo, Mazdak, et al., Nanopore-Based Protein Identification. Journal of the American Chemical Society 144(6):2716-2725 (2022).
Akeson, M, et al., Microsecond time-scale discrimination among polycytidylic acid, polyadenylic acid, and polyuridylic acid as homopolymers or as segments within single RNA molecules. Biophysical Journal 77(6):3227-3233 (1999).
Akopian, Tatos, et al., Processive Degradation of Proteins and Other Catalytic Properties of the Proteasome From Thermoplasma Acidophilum. The Journal of biological chemistry 272(3):1791-1798 (1997).
Aksoyoglu, Alphan, et al., Size-dependent forced PEG partitioning into channels: VDAC, OmpC, and α-hemolysin. Proc Natl Acad Sci U S A 113(32):9003-9008 (2016).
Alfaro, Javier Antonio et al., The Emerging Landscape of Single-molecule Protein Sequencing Technologies. Nature Methods 18:604-617 (2021).
An, Na, et al., Single-molecule investigation of G-quadruplex folds of the human telomere sequence in a protein nanocavity. Proceedings of the National Academy of Sciences of the United States of America 111(40):14325-14331 (2014).
Anderluh, Gregor et al.: Cytolytic peptide and protein toxins from sea anemones (*Anthozoa: Actiniaria*). Toxicon 40(2):111-124 (2002).
André, Ingemar., et al., Prediction of the structure of symmetrical protein assemblies. Proc Natl Acad Sci U S A 104(45):17656-17661 (2007).
Aqvist, et al., Dipoles localized at helix termini of proteins stabilize charges. Proc Natl Acad Sci U S A 88(5):2026-2030 (1991).
Asandei, Alina, et al., Electroosmotic Trap Against the Electrophoretic Force Near a Protein Nanopore Reveals Peptide Dynamics During Capture and Translocation. ACS Applied Materials & Interfaces 8(20):13166-13179 (2016).
Baaken, Gerhard, et al., High-resolution size-discrimination of single nonionic synthetic polymers with a highly charged biological nanopore. ACS Nano 9(6):6443-6449 (2015).
Bacri, Laurent, et al., Discrimination of neutral oligosaccharides through a nanopore. Biochem Biophys Res Commun 412(4):561-564 (2011).
Bakrac, Biserka, et al., Molecular determinants of sphingomyelin specificity of a eukaryotic pore-forming toxin. Journal of Biological Chemistry 283(27):18665-18677 (2008).
Balakrishna, B.H. et al.: Binding of a pleurotolysin ortholog from Pleurotus eryngii to sphingomyelin and cholesterol-rich membrane domains.
Balijepalli, Arvind, et al., Theory of Polymer-nanopore Interactions Refined Using Molecular Dynamics Simulations. Journal of the American Chemical Society 135(18):7064-7072 (2013).
Baniandres; Pablo Martin et al.: Enzyme-less Nanopore Detection of Post-translational Modifications Within Long Polypeptides. Nature Nanotechnology 18:1335-1340 (2023).
Barkow, Sarah R, et al., Polypeptide translocation by the AAA+ ClpXP protease machine. Chemical Biology 16(6):605-612 (2009).
Barlic, Ariana, et al., Lipid Phase Coexistence Favors Membrane Insertion of Equinatoxin-II, a Pore-forming Toxin from Actinia equina. Journal of Biological Chemistry 279(33):34209-34216 (2004).
Bayat, Parisa et. al., Comprehensive Structural Assignment of Glycosaminoglycan Oligo and Polysaccharides by Protein Nanopore. Nature Communications. vol. 13, No. 1 (2022): 12 pages.
Baytshtok, Vladimir, et al., A Structurally Dynamic Region of the HsLU Intermediate Domain Controls Protein Degradation and ATP Hydrolysis. Structure 24(10):1766-1777 (2016).
Becker, Samuel H, et al., Bacterial Proteasomes: Mechanistic and Functional Insights. Microbiology and Molecular Biology Reviews :MMBR 81(1):1-20 (2016).
Bell, Nicholas, Nanopores Formed by DNA Origami: A Review. FEBS letters 588(19):3564-3570 (2014).
Bellomio, Augusto, et al., Purification, Cloning and Characterization of Fragaceatoxin C, a Novel Actinoporin From the Sea Anemone Actinia Fragacea. Toxicon 54(6):869-880 (2009).
Benaroudj, Nadia, et al., ATP hydrolysis by the proteasome regulatory complex PAN serves multiple functions in protein degradation. Molecular cell 1:69-78 (2003).
Beta-channel forming cytolysin—Bacillus cytotoxicus | UniProtKB | UniProt. Accession No. A0A2S1A9G3_9BACI in UniProt 2002-2024.
Bezrukov, S., et al., Dynamics and free energy of polymers partitioning into a nanoscale pore. Macromolecules 29, 8517-8522 (1996).
Biesemans, Annemie., et al., A Protein Rotaxane Controls the Translocation of Proteins Across a ClyA Nanopore. Nano Lett 15(9):6076-6081 (2015).
Boersma, Arnold J, et al., Continuous stochastic detection of amino acid enantiomers with a protein nanopore. Angewandte Chemie International Edition English 51(38):9606-9609 (2012).
Booner, Oscar, et al., Osmotic and Activity Coefficients of Sodium and Potassium Glutamate at 298.15 K. Journal of Chemical & Engineering Data 26:147-148 (1981).
Bouchnak, Imen, et al., Structure, function, and substrates of Clp AAA+ protease systems in cyanobacteria, plastids, and apicoplasts: A comparative analysis. Journal of Biological Chemistry 296:1-16 (2021).
Brauning, Bastian, et al., Structure and mechanism of the two-component α-helical pore-forming toxin YaxAB. Nature communications 9:1-14 (2018).
Brinkerhoff, Henry, et al., Multiple Rereads of Single Proteins at Single-amino Acid Resolution Using Nanopores. Science 374(6574):1509-1513 (2021).
Buchberger, Alexander, et al., Roles of Cdc48 in Regulated Protein Degradation in Yeast. Sub-cellular Biochemistry 66:195-222 (2013).
Burns, Jonathan, et al., Lipid-bilayer-spanning DNA nanopores with a bifunctional porphyrin anchor. Angewandte Chemie 52(46):12069-12072 (2013).
Butler, Tom Z, et al., Single-molecule DNA Detection With An Engineered MspA Protein Nanopore. Proceedings of the National Academy of Sciences of the United States of America 105(52):20647-20652 (2008).
Cao, Chan, et al., Discrimination of oligonucleotides of different lengths with a wild-type aerolysin nanopore. Nature Nanotechnology 11(8):713-718 (2016).
Cao; Chan et al.: Single-molecule sensing of peptides and nucleic acids by engineered aerolysin nanopores. Nature Communications 10: 4918 (2019).

(56) References Cited

OTHER PUBLICATIONS

Castanzo, Dominic, et al., The AAA+ ATPase Msp1 is a Processive Protein Translocase with Robust Unfoldase Activity. Proceedings of the National Academy of Sciences of the United States of America 117(26):14970-14977 (2020).
Chavis, Amy E, et al., Single Molecule Nanopore Spectrometry for Peptide Detection. ACS Sensors 2(9):1319-1328 (2017).
Chen, Baoyu, et al., Engagement of arginine finger to ATP triggers large conformational changes in NtrC1 AAA+ ATPase for remodeling bacterial RNA polymerase. Structure 18(11):1420-1430 (2010).
Chinappi, Mauro, et al., Analytical Model for Particle Capture in Nanopores Elucidates Competition Among Electrophoresis, Electroosmosis, and Dielectrophoresis. ACS Nano 14(11):15816-15828 (2020).
Chinappi, Mauro et al.: Protein sequencing via nanopore based devices: a nanofluidics perspective. Journal of Physics: Condensed Matter, Institute of Physics Publishing, Bristol, GB 30(20):204002 (2018), XP020327001. DOI: 10.1088/1361-648X/AABABE.
Clarke et al., Continuous base identification for single-molecule nanopore DNA sequencing. Nat Nanotechnol. 4(4):265-270 (2009).
Cressiot, Benjamin, et al., Dynamics and Energy Contributions for Transport of Unfolded Pertactin Through a Protein Nanopore. ACS Nano 9(9):9050-61 (2015).
Cressiot, Benjamin, et al., Protein Transport Through a Narrow Solid-state Nanopore at High Voltage: Experiments and Theory. American Chemical Society nano 6(7):6236-6243 (2012).
Cressiot, Benjamin, et al., Thermostable Virus Portal Proteins as Reprogrammable Adapters for Solid-state Nanopore Sensors. Nature Communications 9(4652):1-7 (2018).
Crnković, Ana, et al., Biological Nanopores: Engineering on Demand. Life (Basel) 11(1):27 (2021).
Dal-Peraro, Matteo, et al., Pore-forming toxins: ancient, but never really out of fashion. Nature reviews. Microbiology 14(2):77-92 (2016).
Database UniProt B9W5G6 XP002796191.
Delta-Actitoxin-Aeq1b-like [Orbicella faveolata]. BioProject PRJNA381078, XP-020600665.1. (2017) https://www.ncbi.nlm.nih.gov/protein/1176123762?sat=4&satkey=191642050.
Derrington, Ian M, et al., Nanopore DNA sequencing with MspA. Proceedings of the National Academy of Sciences of the United States of America 107(37):16060-16065 (2010).
Derrington, Ian M. et al.: Subangstrom single-molecule measurements of motor proteins using a nanopore. Nature Biotechnology Sep. 28, 2015.
Dong, Changjiang et al.: The structure of Wza, the translocon for group 1 capsular polysaccharides in *Escherichia coli*, identifies a new class of outer membrane protein. Nature 444(7116):226-229 (2006). doi: 10.1038/nature05267.
Dong, Changjiang, et al., Wza the Translocon for *E. Coli* Capsular Polysaccharides Defines a New Class of Membrane Protein. Nature 444:226-229 (2006).
Dougana, David, et al., AAA+ proteins and substrate recognition, it all depends on their partner in crime. FEBS Letters 529:6-10 (2002).
Effantin, Gregory, et al., Binding of the ClpA Unfoldase Opens the Axial Gate of ClpP Peptidase. The Journal of Biological Chemistry 285(19):14834-14840 (2010).
EP17734851.3 European Examination Report dated Feb. 12, 2020.
EP20206642.9 Extended European Search Report dated May 3, 2021.
Erlandson, Karl, et al., A Role for the Two-helix Finger of the Seca ATPase in Protein Translocation. Nature. vol. 455, 7215:984-987 (2008).
European Patent Application No. EP22204590 European Extended Search Report dated Aug. 14, 2023.
Faller, Michael, et al., The structure of a mycobacterial outer-membrane channel. Science 303(5661):1189-1192 (2004).
Flynn, Julia, et al., Overlapping Recognition Determinants Within the ssrA Degradation Tag Allow Modulation of Proteolysis. Proceedings of the National Academy of Sciences of the United States of America 98(19):10584-10589 (2001).
Forouzan, Dara, et al., The Archaeal Proteasome is Regulated by a Network of AAA ATPases. The Journal of Biological Chemistry 287(46):39254-62 (2012).
Forster, Andreas et al.: The 1.9 Å structure of a proteasome-11S activator complex and implications for proteasome-PAN/PA700 interactions. Molecular Cell 18:589-599 (2005). DOI 10.1016/j.molcel.2005.04.016.
Franceschini, Lorenzo, et al., A nanopore machine promotes the vectorial transport of DNA across membranes. Nature Communications 4(2415): 8 Pages (2013).
Frees, Dorte, et al., Clp ATPases Are Required for Stress Tolerance, Intracellular Replication and Biofilm Formation in *Staphylococcus aureus*. Molecular Microbiology 54(5): 1445-62 (2004).
Furini, Simone, et al., Model-based Prediction of the Alpha-hemolysin Structure in the Hexameric State. Biophysical journal 95 (5): 2265-2274 (2008).
García-Ortega, Lucia, et al., The Behavior of Sea Anemone Actinoporins at the Water-membrane Interface. Biochimica Et Biophysica Acta 1808 (9):2275-2288 (2011).
Gerega, Alexandra, et al., VAT, the Thermoplasma Homolog of Mammalian p97/VCP, Is an N Domain-regulated Protein Unfoldase. The Journal of Biological Chemistry 280(52):42856-42862 (2020).
Gimenez-Andres, Manuel, et al., The Many Faces of Amphipathic Helices. Biomolecules 8(45):1-14 (2018).
Glynn, Steven E, et al., Dynamic and Static Components Power Unfolding in Topologically Closed Rings of a AAA+ Proteolytic Machine. Nature Structural & Molecular Biology 19(6):616-622 (2012).
Gonzalez-Perez, Alfredo, et al., Biomimetic Triblock Copolymer Membrane Arrays: A Stable Template for Functional Membrane Proteins. Langmuir 25(18):10447-10450 (2009).
Gouaux, J,E, et al., Subunit stoichiometry of staphylococcal alpha-hemolysin in crystals and on membranes: a heptameric transmembrane pore. Proceedings of the National Academy of Sciences of the United States of America 91(26): 12828-31 (1994).
Gu, Li-qun, et al., Interaction of the Noncovalent Molecular Adapter, Beta-cyclodextrin, With the Staphylococcal Alpha-hemolysin Pore. Biophysical journal 79(4):1967-75 (2000).
Gu, Li-qun, et al., Stochastic Sensing of Organic Analytes by a Pore-forming Protein Containing a Molecular Adapter. Nature 398:686-690(1999).
Guimaraes, Carla P, et al., Site-specific C-terminal and internal loop labeling of proteins using sortase-mediated reactions. Nature Protocols 8(9):1787-1799 (2013).
Hammerstein, Anne, et al., Subunit Dimers of Alpha-hemolysin Expand the Engineering Toolbox for Protein Nanopores. The Journal of Biological Chemistry 286(16):14324-34 (2011).
Hardy, Simon. P, et al., CytK Toxin of Bacillus Cereus Forms Pores in Planar Lipid Bilayers and is Cytotoxic to Intestinal Epithelia. FEMS Microbiology Letters 197:47-51 (2001).
Hartmann, et al., Low temperature incommensurately modulated and noncollinear spin structure in FeCr2S4. Journal of Physics: Condensed Matter, vol. 22, 5:1-21 (2010).
Henning-Knechtel; Anja et al.: DNA-assisted oligomerization of pore-forming toxin monomers into precisely-controlled protein channels. Nucleic Acids Research 45(21):12057- 12068 (2017).
Heron, Andrew, et al., Simultaneous Measurement of Ionic Current and Fluorescence from Single Protein Pores. Journal of the American Chemical Society 131(5):1652-1653 (2009).
Hille, Bertil, Ion Channels of Excitable Membranes, Third edition. Sinauer Associates Inc 37 Pages (2001).
Ho, Ching-Wen., et al., Engineering a nanopore with co-chaperonin function. Sci Adv 1(11):1-9 (2015).
Horton, Robert, et al. Engineering hybrid genes without the use of restriction enzymes: gene splicing by overlap extension. Gene 77(1):61-68 (1989).
Huang, Gang, et al., Detection of Single Amino Acid Differences in Haemoglobin From Blood Samples Using a Nanopore. ChemRxiv: 24 Pages (2021).
Huang, Gang, et al., Electro-Osmotic Capture and Ionic Discrimination of Peptide and Protein Biomarkers With Frac Nanopores. Nature Communications 8(935): 11 Pages (2017).

(56) References Cited

OTHER PUBLICATIONS

Huang, Gang, et al., Electro-Osmotic Vortices Promote the Capture of Folded Proteins by PlyAB Nanopores. Nano Letters 20(5):3819-3827 (2020).
Huang, Gang et al., FraC nanopores with adjustable diameter identify the mass of opposite-charge peptides with 44 dalton resolution. Nature Communications 10:1-10 (2019).
Huang, Gang, et al., PlyAB Nanopores Detect Single Amino Acid Differences in Folded Haemoglobin From Blood. Angewandte Chemie International Edition 61(34): 8 Pages (2022).
Huang, Kevin: Engineering biological nanopores for proteomics study. University of Groningen (2019). DOI: 10.33612/diss.102598418.
Huang, Rui, et al., Unfolding the mechanism of the AAA+ unfoldase VAT by a combined cryo-EM, solution NMR study. Proceedings of the National Academy of Sciences of the United States of America 1-10 (2016).
Huang, Shuo, et al., High-Throughput Optical Sensing of Nucleic Acids in a Nanopore Array. Nature Nanotechnology 10:986-991 (2015).
Huber, Eva, et al., A Unified Mechanism for Proteolysis and Autocatalytic Activation in the 20s Proteasome. Nature communications 7:1-10 (2016).
Huber, Eva, et al., The mammalian proteasome activator PA28 forms an asymmetric α4B3 complex. Structure 25(10):1473-1480 (2017).
Humbard, Matthew A, et al., Ubiquitin-like Small Archaeal Modifier Proteins (SAMPs) in Haloferax Volcanii. Nature 463:54-60 (2010).
Ivanov, Aleksandar P, et al., DNA tunneling detector embedded in a nanopore. Nano Letters 11(1):279-285 (2011).
Jiang, Jiansen, et al., Atomic structure of anthrax protective antigen pore elucidates toxin translocation. Nature 521(7553):545-549 (2015).
Kasianowicz, J.J, et al., Characterization of individual polynucleotide molecules using a membrane channel. Proceedings of the National Academy of Sciences of the United States of America 93(24):13770-13773 (1996).
Kavalchuk, Mikhail, et al., Structural Basis of Prokaryotic Ubiquitin-like Protein Engagement and Translocation by the Mycobacterial Mpa-proteasome Complex. Nature Communications 13(1):276 (2022).
Kennedy, Eamonn., et al., Reading the primary structure of a protein with 0.07 nm3 resolution using a subnanometre-diameter pore. Nat Nanotechnol 11(11):968-976 (2016).
Kim, Yong-In, et al., Dynamics of Substrate Denaturation and Translocation by the Clpxp Degradation Machine. Molecular cell 5(4):639-648 (2000).
Kisselev, Alexei, et al., Why Does Threonine, and Not Serine, Function as the Active Site Nucleophile in Proteasomes?. The Journal of Biological Chemistry 275(20):14831-14837 (2000).
Kowalczyk, Stefan W, et al., Detection of Local Protein Structures Along DNA Using Solid-state Nanopores. Nano Letters 10(1):324-328 (2010).
Krasilnikov, Oleg V, et al., Single Polymer Molecules in a Protein Nanopore in the Limit of a Strong Polymer-Pore Attraction. Physical Review Letters 97(1): 4 Pages (2006).
Kravats, Andrea, et al., Unfolding and translocation pathway of substrate protein controlled by structure in repetitive allosteric cycles of the ClpY ATPase. Proceedings of the National Academy of Sciences of the United States of America 108(6):2234-2239 (2011).
Krishnan R, Smrithi, et al., Autonomously Assembled Synthetic Transmembrane Peptide Pore. Journal of the American Chemical Society 141(7):2949-2959 (2019).
Krishnan Smrithi et al., Designed Alpha-helical Barrels for Charge-selective Peptide Translocation. Chemical Science 12(2):639-649 (2021).
Kristan, Katarina Crnigoj, et al., Molecular Mechanism of Pore Formation by Actinoporins. Toxicon 54(8):1125-34 (2009).
Kuehn et al., Proteasome activator PA28 and its interaction with 20 S proteasomes. Archives of biochemistry and biophysics 329(1):87-96 (1996).
Lamichhane, Usha, et al., Peptide translocation through the mesoscopic channel: binding kinetics at the single molecule level. Eur Biophys J 42(5):363-369 (2013).
Langklotz, Sina, et al., Structure and Function of the Bacterial AAA Protease FtsH. Biochim Biophys Acta 1823(1):40-48 (2012).
Laszlo, Andrew H, et al., Decoding long nanopore sequencing reads of natural DNA. Nature Biotechnology 32(8):829-833 (2014).
Li, Bisheng, et al., Black Phosphorus, a Rising Star 2D Nanomaterial in the Post-Graphene Era: Synthesis, Properties, Modifications, and Photocatalysis Applications. Small 15:1-30 (2019).
Li, et al., Detection of Peptides with Different Charges and Lengths by Using the Aerolysin Nanopore.4, 1-5 (2018).
Li, Jianfeng, et al., A comparative study of point-to-point algorithms for matching spectra. Chemometrics and Intelligent Laboratory Systems 82(1-2): 50-58 (2006).
Lide, David R, et al., CRC Handbook of Chemistry and Physics, 84th edition. Journal of the American Chemical Society 126(5):1585-1588 (2003).
Liu, Huanting, et al., An Efficient One-step Site-directed Deletion, Insertion, Single and Multiple-site Plasmid Mutagenesis Protocol. BMC biotechnology 8:91 (2008).
Liu, Wenxing et. al., Probing Protein Nanopores With Poly Ethylene Glycols. Proteomics. vol. 22, No. 5-6 (2022): 16 pages.
Liu, Xi, et al., High Expression of Nfat2 Contributes to Carboplatin Resistance in Lung Cancer. Experimental and Molecular Pathology 110:104290 (2019).
Lowe, Jan, et al., Crystal structure of the 20S Proteasome From the archaeon T. acidophilum at 3.4 A resolution. Science 268(5210):533-539 (1995).
Lucas, Florian Leonardus Rudolfus, et al., The Manipulation of the Internal Hydrophobicity of FraC Nanopores Augments Peptide Capture and Recognition. ACS Nano 15(6):9600-9613 (2021).
Ma, Wenzhe, et al., Specificity of Trypsin and Chymotrypsin: Loop-motion-controlled Dynamic Correlation as a Determinant. Biophysical journal 89 (2):1183-1193 (2005).
Macrander, Jason, et al., Evolution of the Cytolytic Pore-Forming Proteins (Actinoporins) in Sea Anemones. Toxins 8(12):1-16 (2016).
Maglia, Giovanni, et al., Analysis of Single Nucleic Acid Molecules With Protein Nanopores. Methods in Enzymology 475:591-623 (2010).
Maglia, Giovanni, et al., Enhanced translocation of single DNA molecules through alpha-hemolysin nanopores by manipulation of internal charge. Proceedings of the National Academy of Sciences of the United States of America 105(50):19720-19725 (2008).
Maillard, Rodrigo A, et al., ClpX(P) Generates Mechanical Force to Unfold and Translocate Its Protein Substrates. Cell 145(3):459-469 (2011).
Manning, Gerald S, The Persistence Length of DNA is Reached From the Persistence Length of Its Null Isomer Through an Internal Electrostatic Stretching Force. Biophysical Journal 91(10):3607-3616 (2006).
Manrao, Elizabeth A, et al., Nucleotide discrimination with DNA immobilized in the MspA nanopore. PLOS One 6(10): 7 Pages (2011).
Manrao, Elizabeth, et al., Reading DNA at Single-nucleotide Resolution With a Mutant MspA Nanopore and phi29 DNA Polymerase. Nature Biotechnology 30(4):349-353 (2012).
Martin, Andreas, et al., Pore Loops of the AAA+ ClpX Machine Grip Substrates to Drive Translocation and Unfolding. Nature Structural & Molecular Biology 15(11):1147-1151 (2008).
Martin, Andreas, et al., Rebuilt AAA + Motors Reveal Operating Principles for ATP-Fuelled Machines. Nature 437:1115-1120 (2005).
Mathe, Jerome, et al., Nanopore unzipping of individual DNA hairpin molecules. Biophysical Journal 87(5):3205-3212 (2004).
Mechaly; Ariel E. et al.: Structural Insights into the Oligomerization and Architecture of Eukaryotic Membrane Pore-Forming Toxins. Structure 19:181-191 (2011).
Merstorf, Celine, et al., Wild Type, Mutant Protein Unfolding and Phase Transition Detected By Single-nanopore Recording. ACS Chemical Biology 7(4):652-658 (2012).

(56) References Cited

OTHER PUBLICATIONS

Mesa-Galloso, Haydee et al.: Disrupting a key hydrophobic pair in the oligomerization interface of the actinoporins impairs their pore-forming activity. Protein Science 26:550-565 (2017). https://onlinelibrary.wiley.com/doi/full/10.1002/pro.3104.
Miethke, Marcus, et al., Involvement of Bacillus Subtilis ClpE in CtsR Degradation and Protein Quality Control. Journal of Bacteriology 188(13):4610-4619 (2006).
Miles, George, et al., Assembly of the Bi-component Leukocidin Pore Examined by Truncation Mutagenesis. The Journal of Biological Chemistry 281(4):2205-14 (2006).
Miles, George, et al., The Staphylococcal Leukocidin Bicomponent Toxin Forms Large Ionic Channels. Biochemistry 40(29):8514-8522 (2001).
Mishra, Ribhav, et al., Proteasome-mediated Proteostasis: Novel Medicinal and Pharmacological Strategies for Diseases. Medicinal Research Reviews 38(6):1916-1973 (2018).
Mitchell, Jonathan, et al., Sequence-Dependent Persistence Lengths of DNA. Journal of Chemical Theory and Computation 13(4):1539-1555 (2017).
Mohammad, Mohammad, et al., Controlling a single protein in a nanopore through electrostatic traps. 130(12):4081-4088 (2008).
Morante, Koldo, et al., A Pore-Forming Toxin Requires a Specific Residue for Its Activity in Membranes with Particular Physicochemical Properties. Journal of Biological Chemistry 290(17):10850-10861 (2015).
Morante, Koldo et al.: Functional characterization of Val60, a key residue involved in the membrane-oligomerization of fragaceatoxin C, an actinoporin from Actinia fragacea. FEBS Letters 589(15):1840-1846 (2015). https://doi.org/10.1016/j.febslet.2015.06.012.
Motone; Keisuke et al.: Herding cats: Label-based approaches in protein translocation through nanopore sensors for single-molecule protein sequence analysis. Science 24:103032 (2021).
Motone, Keisuke et al., Multi-pass, Single-molecule Nanopore Reading of Long Protein Strands With Single-amino Acid Sensitivity. bioRxiv : The Preprint Server for Biology (2023): 47 pages.
Motone; Keisuke et al.: Not if but when nanopore protein sequencing meets single-cell proteomics. Nature Methods 20:336-338 (2023).
Movileanu, Liviu, et al., Interactions of peptides with a protein pore. Biophysical Journal 89(2):1030-1045 (2005).
Movileanu, Liviu, et al., Interrogating single proteins through nanopores: challenges and opportunities. Trends in Biotechnology 27(6):333-341 (2009).
Muccio, Giovanni Di, et al., Geometrically Induced Selectivity and Unidirectional Electroosmosis in Uncharged Nanopores. ACS Nano 16(6):8716-8728 (2022).
Mullner, Daniel, et al., fastcluster: Fast Hierarchical, Agglomerative Clustering Routines for R and Python. Journal of Statistical Software 53(9): 1-18 (2013).
Niitsu: Al et al.: Membrane-spanning $\alpha$-helical barrels as tractable protein-design targets. Phil. Trans. R. Soc. B 372:20160213 (2016).
Nivala, Jeff, et al., Discrimination Among Protein Variants Using An Unfoldase-coupled Nanopore. ACS Nano 8(12):12365-12375 (2014).
Nivala, Jeff, et al., Unfoldase-mediated Protein Translocation Through An $\alpha$-hemolysin Nanopore. Nature Biotechnology 31(3):247-250 (2013).
Noakes, Matthew, et al., Increasing the Accuracy of Nanopore DNA Sequencing Using a Time-varying Cross Membrane Voltage. Nature Biotechnology 37(6):651-656 (2019).
Nouwen, Nico, et al., Charged Amino Acids in a Preprotein Inhibit SecA-dependent Protein Translocation. Journal of Molecular Biology 386(4):1000-1010 (2009).
Nuijens, Timo, et al., Engineering a Diverse Ligase Toolbox for Peptide Segment Condensation. Advanced Synthesis and catalysis 358: 9 Pages (2016).
Olivare, Adrian, et al., Mechanistic insights into bacterial AAA+ proteases and protein-remodelling machines. Nature reviews. Microbiology, vol. 14(1):33-44(2016).
Ortega, Joaquin, et al., Visualization of Substrate Binding and Translocation by the Atp-dependent Protease, ClpXp, Molecular cell 6(6):1515-1521 (2000).
Oukhaled, Abdel., et al., Transport of long neutral polymers in the semidilute regime through a protein nanopore. Phys Rev Lett 108(8):1-4 (2012).
Oukhaled, G, et al., Unfolding of Proteins and Long Transient Conformations Detected by Single Nanopore Recording. Physical review letters 98(15):158101 (2007).
Pastoriza-Gallego, Manuela, et al., Evidence of Unfolded Protein Translocation through a Protein Nanopore. ACS Nano 8(11):11350-11360 (2014).
Pavlenok, Mikhail, et al., Control of Subunit Stoichiometry in Single-chain MspA Nanopores. Biophysical Journal 121(5):742-754 (2022).
PCT/NL2017/050331 International Search Report and Written Opinion dated Sep. 5, 2017.
PCT/NL2019/050588 International Search Report and Written opinion dated Dec. 17, 2019 (Pub. No. WO2020055246).
PCT/NL2020/050726 International Search Report and Written Opinion dated Feb. 19. 2021.
PCT/NL2022/050266 International Search Report dated Nov. 28, 2022.
PCT/NL2023/050568 International Search Report dated Jan. 24, 2024.
Piguet, Fabien, et al., Identification of single amino acid differences in uniformly charged homopolymeric peptides with aerolysin nanopore. Nature communications 9(966):1-13 (2018).
Purnell, Robert F, et al., Discrimination of single base substitutions in a DNA strand immobilized in a biological nanopore. ACS Nano 3(9):2533-2538 (2009).
QIAO Dan et al., Synthetic Macrocycle Nanopore for Potassium-Selective Transmembrane Transport. Journal of the American Chemical Society 143(39):15975-15983 (2021).
Rincon-Restrepo, Marcela., et al., Controlled translocation of individual DNA molecules through protein nanopores with engineered molecular brakes. 11(2):746-750 (2011).
Ripstein, Zev, et al., Structure of a AAA+ unfoldase in the process of unfolding substrate. eLife 6:e25754 (2017).
Robertson, Joseph W F, et al., Nanopore Sensing: a Physical-chemical Approach. Biochimica Et Biophysica Acta. Biomembranes 1863 (9):1-15 (2021).
Robertson, Joseph W F, et al., Single-molecule mass spectrometry in solution using a solitary nanopore. Proceedings of the National Academy of Sciences of the United States of America 104(20):8207-8211 (2007).
Rodriguez-Vazquez, Nuria, et al., Membrane-targeted Self-assembling Cyclic Peptide Nanotubes. Current Topics in Medicinal Chemistry 14(23):2647-61 (2014).
Rojko, Nejc et al.: Pore Formation by Actinoporins, Cytolysins From Sea Anemones. Biochimica et Biophysica Acta 1858(3):446-456 (2016).
Ros, Uris, et al., Differences in Activity of Actinoporins Are Related With the Hydrophobicity of Their N-Terminus. Biochimie 116:70-78 (2015).
Rosen, Christian B, et al., Single-molecule Site-specific Detection of Protein Phosphorylation With a Nanopore. Nature Biotechnology 32(2):179-181 (2014).
Rosen, Christian B, et al., Targeting the N Terminus for Site-selective Protein Modification. Nature Chemical Biology 13(7):697-705 (2017).
Sauciuc Adina et al., An Engineered Electroosmotic Flow Transports Unravelled Proteins Across Nanopores. bioRxiv (2023).
Sauciuc, Adina et al., Translocation of Linearized Full-length Proteins Through an Engineered Nanopore Under Opposing Electrophoretic Force. Nature Biotechnology (2023): 63 pages.
Sauer, Rolf, et al., Preoperative Versus Postoperative Chemoradiotherapy for Rectal Cancer. The New England Journal of Medicine. 351(17):1731-1740 (2004).
Schmidt, Bernhard, Hydrophilic Polymers. Polymers (Basel) 11(4): 693 (2019).

(56) References Cited

OTHER PUBLICATIONS

Schon, Peter, et al., Equinatoxin II Permeabilizing Activity Depends on the Presence of Sphingomyelin and Lipid Phase Coexistence. Biophysical Journal 95(2):691-698 (2008).
Scott, Alistair, et al., Constructing Ion Channels From Water-soluble A-helical Barrels. Nature chemistry 13(7):643-650 (2021).
Seemüller, Erika, et al., Proteasome From Thermoplasma Acidophilum: A Threonine Protease. Science 268(5210):579-82 (1995).
Serek-Heuberger, Justyna, et al., Two Unique Membrane-bound Aaa Proteins From Sulfolobus Solfataricus. Biochemical Society Transactions 37(1):118-122 (2009).
Shimizu, Keisuke, et al., De Novo Design of a Nanopore for Single-molecule Detection That Incorporates a β-hairpin Peptide. Nature Nanotechnology 17(1):67-75 (2022).
Shuang, Li et al.: Detection of peptides with different charge and length by aerolysin nanopore. ChemElectroChem 6(1):126-129 (2018. https://doi.org/10.1002/celc.201800288.
Singh, Satyendra, et al., Functional Domains of the ClpA and ClpX Molecular Chaperones Identified by Limited Proteolysis and Deletion Analysis. The Journal of Biological Chemistry 276(31):29420-29429 (2001).
Soskine, Misha, et al., Single-molecule Analyte Recognition With Clya Nanopores Equipped With Internal Protein Adaptors. Journal of the American Chemical Society 137(17):5793-5797 (2015).
Soskine, Misha, et al., Tuning the size and properties of ClyA nanopores assisted by directed evolution. Journal of the American Chemical Society 135(36):13456-13463 (2013).
Spaan, András, et al., Leukocidins: staphylococcal bi-component pore-forming toxins find their receptors. Nature reviews. Microbiology 15(7):435-447 (2019).
Spruijt, Evan, et al., DNA scaffolds support stable and uniform peptide nanopores. Nature Nanotechnology 13:739-745 (2018).
Stadtmueller, Beth M. et al.: Proteasome Activators. Molecular Cell 41:8-19 (2011).
Stefureac, Radu, et al., Nanopore Analysis of a Small 86-residue Protein. Small 4(1):59-63 (2008).
Stefureac, Radu, et al., Transport of Alpha-helical Peptides Through Alpha-hemolysin and Aerolysin Pores. Biochemistry 45(30):9172-9 (2006).
Stoddart, David., et al., DNA stretching and optimization of nucleobase recognition in enzymatic nanopore sequencing Nanotechnology 26(8):10-16 (2015).
Stoddart, David, et al., Functional Truncated Membrane Pores. Proceedings of the National Academy of Sciences of the United States of America 111(7):2425-2430 (2014).
Stoddart, David, et al., Multiple base-recognition sites in a biological nanopore: two heads are better than one. Angewandte Chemie International Edition English 49(3):556-559 (2010).
Stoddart, David, et al., Nucleobase recognition in ssDNA at the central constriction of the alpha-hemolysin pore. Nano Letters 10(9):3633-3637 (2010).
Stoddart, David, et al., Single-nucleotide discrimination in immobilized DNA oligonucleotides with a biological nanopore. Proceedings of the National Academy of Sciences of the United States of America 106(19):7702-7707 (2009).
Stranges, Benjamin, et al., Design and Characterization of a Nanopore-coupled Polymerase for Single-molecule Dna Sequencing by Synthesis on an Electrode Array. Proceedings of the National Academy of Sciences of the United States of America 113(44):E6749-E6756 (2016).
Stryer: Biochemistry 4th Ed. Wh Freeman, New York. p. 18-23 (1995).
Sugiyama, Masaaki, et al., Spatial Arrangement and Functional Role of a Subunits of Proteasome Activator Pa28 in Hetero-oligomeric Form. Biochemical and biophysical research communications 432:141-145 (2013).
Suzuki, Carolyn K, et al., Functional Mechanics of the ATP-dependent Lon Protease-Lessons From Endogenous Protein and Synthetic Peptide Substrates. Biochimica Et Biophysica Acta 1784(5):727-35 (2008).
Talaga, David S, et al., Single-molecule Protein Unfolding in Solid State Nanopores. Journal of the American Chemical Society 131(26):9287-9297 (2009).
Tanaka, Koji, et al., Bidirectional Transformation of a Metamorphic Protein between the Water-Soluble and Transmembrane Native States. Biochemistry 54(46):6863-6866 (2015).
Tanaka, Koji et al.: Structural Basis for Self-assembly of a Cytolytic Pore Lined by Protein and Lipid. Nature Communications 6: 6337 (2015).
Thapa, Parashar, et al., Native chemical ligation: a boon to peptide chemistry. Molecules 19(9): 14461-83 (2014).
Too, Priscilla Hiu-mei, et al., Slippery Substrates Impair Function of a Bacterial Protease ATPase by Unbalancing Translocation Versus Exit. The Journal of Biological Chemistry 288(19):13243-57 (2013).
Toplak, Ana, et al., Peptiligase an Enzyme for efficient Chemoenzymatic peptide Synthesis and Cyclization in Water. Advanced Synthesis and catalysis 358:2140-2147 (2016).
Tsutsui, Makusu, et al., Sparse Multi-nanopore Osmotic Power Generators. Cell Press Physical Science 3:1-12 (2022).
UniProt XP 002796191, Review, 2009.
U.S. Appl. No. 16/317,119 Office Action dated Apr. 28, 2021.
Van Der Verren, Sander E, et al., A Dual-constriction Biological Nanopore Resolves Homonucleotide Sequences With High Fidelity. Nature biotechnology 38:1415-1420 (2020).
Versloot, Roderick Corstiaan Abraham, et al., β-Barrel Nanopores with an Acidic-Aromatic Sensing Region Identify Proteinogenic Peptides at Low pH. ACS Nano 16(5):7258-7268 (2022).
Vorobieva, Anastassia A, De Novo Design of Transmembrane β Barrels. Science 371(6531): 1-25 (2021).
Wang, Jimin, et al., The structure of ClpP at 2.3 A resolution suggests a model for ATP-dependent proteolysis. Cell 91(4):447-456 (1997).
Wanunu, Meni, et al., DNA translocation governed by interactions with solid-state nanopores. Biophys J 95(10):4716-4725 (2008).
Wanunu, Meni., et al., Electrostatic focusing of unlabelled DNA into nanoscale pores using a salt gradient. Nat Nanotechnol 5(2):160-165 (2010).
Watanabe, Hirokazu, et al., Analysis of Pore Formation and Protein Translocation Using Large Biological Nanopores. Analytical Chemistry 89(21):11269-11277 (2017).
Wei, Bryan, et al., Complex Shapes Self-assembled From Single-stranded DNA tiles. Nature 485(7400):623-626 (2012).
Wendell, David, et al., Translocation of double-stranded DNA through membrane-adapted phi29 motor protein nanopores. Nature Nanotechnology 4(11):765-72 (2009).
Wilson, Jason S et al.: Identification and structural analysis of the tripartite α-pore forming toxin of Aeromonas hydrophila. Nature Communications 10:2900 (2019).
Wloka, Carsten, et al., Alpha-Helical Fragaceatoxin C Nanopore Engineered for Double-Stranded and Single-Stranded Nucleic Acid Analysis. Angewandte Chemie 55(40):12494-12498 (2016).
Wong, C T A, et al., Polymer Capture by Electro-osmotic Flow of Oppositely Charged Nanopores. The Journal of chemical physics 126(16):164903 (2007).
Xue, Liang, et al., Solid-state Nanopore Sensors. Nature Reviews Materials 21 Pages (2020).
Ye, Cheng, et al., Pandemic-scale Phylogenetics. bioRxiv : the preprint server for biology 1-16 (2021).
Ying, Yi-Lun, et al., Handling A Protein With a Nanopore Machine. Nature Chemistry 13:1160-1162 (2021).
Yu, Luning et al.: Unidirectional Single-File Transport of Full-Length Proteins Through a Nanopore. Nature Biotechnology 41:1130-1139 (2023).
Yusupov, Marat, et al., Crystal Structure of the Ribosome at 5.5 a Resolution. Science 292(5518):883-896 (2001).
Zhang, Shengli, et al., Bottom-up Fabrication of a Proteasome-nanopore That Unravels and Processes Single Proteins. Nature Chemistry 13(12):1192-1199 (2021).
Zhao, Qitao, et al., Study of Peptide Transport Through Engineered Protein Channels. The Journal of Physical Chemistry B 133 (11):3572-3578 (2009).

(56) References Cited

OTHER PUBLICATIONS

Zhao, Yanan, et al., Single Molecule Spectroscopy of Amino Acids and Peptides by Recognition Tunneling. Nature Nanotechnology 9(6):466-473 (2014).
Zhao, Yingqi, et al., Label-Free Optical Analysis of Biomolecules in Solid-State Nanopores: Toward Single-Molecule Protein Sequencing. ACS Photonics 9:730-742 (2022).
Ziemski, Michal, et al., Cdc48-Like Protein of Actinobacteria (Cpa) is a Novel Proteasome Interactor in Mycobacteria and Related Organisms. Elife 29(7):e34055 (2018).
Cajado-Carvalho, Daniela et al. Insights into the Hypertensive Effects of Tityus serrulatus Scorpion Venom: Purification of an Angiotensin-Converting Enzyme-Like Peptidase. Toxins 8(12)348:1-16 (2016).
Garcia-Ortega, Lucia et al. The behavior of sea anemone actinoporins at the water-membrane interface. Biomembranes 1808(9):2275-2288 (2011).
GenPept: DELTA-Actitoxin-Aeq1b-like [Orbicella faveolata]. NBCI Reference Sequence: XP_020600665.1. (2017) https://www.ncbi.nlm.nih.gov/protein/1176123762?sat=4&satkey=191642050.
Gu, Li-qun et al. Electroosmotic Enhancement of the Binding of a Neutral Molecule to a Transmembrane Pore. PNAS USA 100(26):15498-15503 (2003).
Huang, Kevin. Engineering Biological Nanopores for Proteomics Study. University of Groningen: 39 Pages (2019).
Lucas, Florian Leonardus Rudolfus, et al., Protein identification by nanopore peptide profiling. Nature Communications 12(1):5795 (2021).
NCBI Reference Sequence: XP_020600665.1, DELTA-actitoxin-Aeq1b-like [Orbicella faveolata] (2017).
PCT/NL2023/050570 International Search Report and Written Opinion dated Apr. 5, 2024.
Robertson, Joseph W.F. et al. Nanopore sensing: A physical-chemical approach. Biochimica et Biophysica Acta (BBA)—Biomembranes 1863(9):183644 (2021).
U.S. Appl. No. 17/269,771 Office Action dated Feb. 9, 2024.
U.S. Appl. No. 18/394,833 Office Action dated Sep. 17, 2024.
U.S. Appl. No. 18/394,975 Office Action dated Apr. 18, 2024.
U.S. Appl. No. 18/394,975 Office Action dated Jul. 16, 2024.
Vorobieva, Anastassia, et al., De Novo Design of Transmembrane B Barrels. Science 371(6531):eabc8182 (2021).
Wallace et al. Identification of epigenetic DNA modifications with a protein nanopore. Chemical Communications 46:8195-8197 (2010).
Weber, Daniel K. et al. Characterization of the Lipid-Binding Site of Equinatoxin II by NMR and Molecular Dynamics Simulation. Biophysical Journal 108(8):1987-1996 (2015).
Zang, Shengli et al., Bottom-up fabrication of a multi-component nanopore sensor that unfolds, processes and recognizes single proteins. Available at https://www.biorxiv.org/content/biorxiv/early/2020/12/06/2020.12.04.411884.full.pdf BioRxiv (pp. 1-50) (2020).
PCT/NL2023/050568 International Preliminary Report on Patentability dated May 8, 2025.
PCT/NL2023/050570 International Preliminary Report on Patentability dated May 8, 2025.
PCT/NL2023/050570 Invitation to Pay Additional Fees dated Feb. 8, 2024.
Tanaka, Koji et al., Haemolytic actinoporins interact with carbohydrates using their lipid-binding module, Philos Trans R Soc Lond B Biol Sci., 372 (2016).
Martin, et al. Protein unfolding by a AAA+ protease is dependent on ATP-hydrolysis rates and substrate energy landscapes. Nature Structural & Molecular Biology. 15(2):139-145 (2008).
U.S. Appl. No. 17/777,757 Office Action dated Jul. 16, 2025.
U.S. Appl. No. 18/394,833 Office Action dated Jul. 16, 2025.

* cited by examiner

A

B

SEQUENCE LISTING

<160> NUMBER OF SEQ ID NOS: 15

<210> SEQ ID NO 1
<211> LENGTH: 60
<212> TYPE: DNA
<213> ORGANISM: Artificial Sequence
<220> FEATURE:
<223> OTHER INFORMATION: oligo I
<220> FEATURE:
<221> NAME/KEY: misc_difference
<222> LOCATION: (1)..(1)
<223> OTHER INFORMATION: biotin group conjugated

<400> SEQUENCE: 1
aaaaaaaaaa aaaaaaaaaa gtgctacgac tctctgtgtg cccccccccc cccccccccc 60

<210> SEQ ID NO 2
<211> LENGTH: 20
<212> TYPE: DNA
<213> ORGANISM: Artificial Sequence
<220> FEATURE:
<223> OTHER INFORMATION: oligo II

<400> SEQUENCE: 2
cacacagaga gtcgtagcac 20

<210> SEQ ID NO 3
<211> LENGTH: 40
<212> TYPE: DNA
<213> ORGANISM: Artificial Sequence
<220> FEATURE:
<223> OTHER INFORMATION: oligonucleotide

<400> SEQUENCE: 3
atatatatat ccatggcgag cgccgatgtc gcgggtgcgg 40

<210> SEQ ID NO 4
<211> LENGTH: 43
<212> TYPE: DNA
<213> ORGANISM: Artificial Sequence
<220> FEATURE:
<223> OTHER INFORMATION: oligonucleotide

<400> SEQUENCE: 4
atatatatat aagcttatca gtgatggtgg tgatgatgcg cag 43

<210> SEQ ID NO 5
<211> LENGTH: 52
<212> TYPE: DNA
<213> ORGANISM: Artificial Sequence
<220> FEATURE:
<223> OTHER INFORMATION: oligonucleotide

<400> SEQUENCE: 5
gccgatgtcg cgggtgcggt aatccgtggt gcgggtctgg gctttgacgt ac 52

<210> SEQ ID NO 6
<211> LENGTH: 26
<212> TYPE: DNA
<213> ORGANISM: Artificial Sequence
<220> FEATURE:
<223> OTHER INFORMATION: oligonucleotide
<220> FEATURE:
<221> NAME/KEY: misc_difference
<222> LOCATION: (1)..(1)
<223> OTHER INFORMATION: biotin group conjugated

<400> SEQUENCE: 6
atatataaaa aaaaaaaaaa aaaaaa 26

<210> SEQ ID NO 7
<211> LENGTH: 26
<212> TYPE: DNA
<213> ORGANISM: Artificial Sequence
<220> FEATURE:
<223> OTHER INFORMATION: oligonucleotide
<220> FEATURE:
<221> NAME/KEY: misc_difference
<222> LOCATION: (1)..(1)
<223> OTHER INFORMATION: biotin group conjugated

<400> SEQUENCE: 7
atatatcccc cccccccccc cccccc 26

<210> SEQ ID NO 8
<211> LENGTH: 26
<212> TYPE: DNA
<213> ORGANISM: Artificial Sequence
<220> FEATURE:
<223> OTHER INFORMATION: oligonucleotide
<220> FEATURE:
<221> NAME/KEY: misc_difference
<222> LOCATION: (1)..(1)
<223> OTHER INFORMATION: biotin group conjugated

<400> SEQUENCE: 8
atatattttt tttttttttt tttttt 26

<210> SEQ ID NO 9
<211> LENGTH: 19
<212> TYPE: DNA
<213> ORGANISM: Artificial Sequence
<220> FEATURE:
<223> OTHER INFORMATION: primer

<400> SEQUENCE: 9
gctagttatt gctcagcgg 19

<210> SEQ ID NO 10
<211> LENGTH: 20
<212> TYPE: DNA
<213> ORGANISM: Artificial Sequence
<220> FEATURE:
<223> OTHER INFORMATION: primer

<400> SEQUENCE: 10
taatacgact cactataggg 20

<210> SEQ ID NO 11
<211> LENGTH: 580
<212> TYPE: DNA
<213> ORGANISM: Actinia fragacea
<220> FEATURE:
<221> NAME/KEY: CDS

```
<222> LOCATION: (1)..(579)

<400> SEQUENCE: 11

atg gcg agc gcc gat gtc gcg ggt gcg gta atc gac ggt gcg ggt ctg       48
Met Ala Ser Ala Asp Val Ala Gly Ala Val Ile Asp Gly Ala Gly Leu
1               5                   10                  15

ggc ttt gac gta ctg aaa acc gtg ctg gag gcc ctg ggc aac gtt aaa       96
Gly Phe Asp Val Leu Lys Thr Val Leu Glu Ala Leu Gly Asn Val Lys
            20                  25                  30

cgc aaa att gcg gta ggg att gat aac gaa tcg ggc aag acc tgg aca      144
Arg Lys Ile Ala Val Gly Ile Asp Asn Glu Ser Gly Lys Thr Trp Thr
        35                  40                  45

gcg atg aat acc tat ttc cgt tct ggt acg agt gat att gtg ctc cca      192
Ala Met Asn Thr Tyr Phe Arg Ser Gly Thr Ser Asp Ile Val Leu Pro
    50                  55                  60

cat aag gtg gcg cat ggt aag gcg ctg ctg tat aac ggt caa aaa aat      240
His Lys Val Ala His Gly Lys Ala Leu Leu Tyr Asn Gly Gln Lys Asn
65                  70                  75                  80

cgc ggt cct gtc gcg acc ggc gta gtg ggt gtg att gcc tat agt atg      288
Arg Gly Pro Val Ala Thr Gly Val Val Gly Val Ile Ala Tyr Ser Met
                85                  90                  95

tct gat ggg aac aca ctg gcg gta ctg ttc tcc gtg ccg tac gat tat      336
Ser Asp Gly Asn Thr Leu Ala Val Leu Phe Ser Val Pro Tyr Asp Tyr
            100                 105                 110

aat tgg tat agc aat tgg tgg aac gtg cgt gtc tac aaa ggc cag aag      384
Asn Trp Tyr Ser Asn Trp Trp Asn Val Arg Val Tyr Lys Gly Gln Lys
        115                 120                 125

cgt gcc gat cag cgc atg tac gag gag ctg tac tat cat cgc tcg ccg      432
Arg Ala Asp Gln Arg Met Tyr Glu Glu Leu Tyr Tyr His Arg Ser Pro
    130                 135                 140

ttt cgc ggc gac aac ggt tgg cat tcc cgg ggc tta ggt tat gga ctc      480
Phe Arg Gly Asp Asn Gly Trp His Ser Arg Gly Leu Gly Tyr Gly Leu
145                 150                 155                 160

aaa agt cgc ggc ttt atg aat agt tcg ggc cac gca atc ctg gag att      528
Lys Ser Arg Gly Phe Met Asn Ser Ser Gly His Ala Ile Leu Glu Ile
                165                 170                 175

cac gtt acc aaa gca ggc tct gcg cat cat cac cac cat cac tga taa      576
His Val Thr Lys Ala Gly Ser Ala His His His His His His
            180                 185                 190

gct t                                                                580
Ala


<210> SEQ ID NO 12
<211> LENGTH: 190
<212> TYPE: PRT
<213> ORGANISM: Actinia fragacea

<400> SEQUENCE: 12

Met Ala Ser Ala Asp Val Ala Gly Ala Val Ile Asp Gly Ala Gly Leu
1               5                   10                  15

Gly Phe Asp Val Leu Lys Thr Val Leu Glu Ala Leu Gly Asn Val Lys
            20                  25                  30

Arg Lys Ile Ala Val Gly Ile Asp Asn Glu Ser Gly Lys Thr Trp Thr
        35                  40                  45

Ala Met Asn Thr Tyr Phe Arg Ser Gly Thr Ser Asp Ile Val Leu Pro
    50                  55                  60

His Lys Val Ala His Gly Lys Ala Leu Leu Tyr Asn Gly Gln Lys Asn
65                  70                  75                  80

Arg Gly Pro Val Ala Thr Gly Val Val Gly Val Ile Ala Tyr Ser Met
```

```
                85                  90                  95

Ser Asp Gly Asn Thr Leu Ala Val Leu Phe Ser Val Pro Tyr Asp Tyr
            100                 105                 110

Asn Trp Tyr Ser Asn Trp Trp Asn Val Arg Val Tyr Lys Gly Gln Lys
        115                 120                 125

Arg Ala Asp Gln Arg Met Tyr Glu Glu Leu Tyr Tyr His Arg Ser Pro
    130                 135                 140

Phe Arg Gly Asp Asn Gly Trp His Ser Arg Gly Leu Gly Tyr Gly Leu
145                 150                 155                 160

Lys Ser Arg Gly Phe Met Asn Ser Ser Gly His Ala Ile Leu Glu Ile
                165                 170                 175

His Val Thr Lys Ala Gly Ser Ala His His His His His His
            180                 185                 190


<210> SEQ ID NO 13
<211> LENGTH: 190
<212> TYPE: PRT
<213> ORGANISM: Actinia fragacea
<220> FEATURE:
<221> NAME/KEY: BINDING
<222> LOCATION: (185)..(190)
<223> OTHER INFORMATION: His(6)-tag

<400> SEQUENCE: 13

Met Ala Ser Ala Asp Val Ala Gly Ala Val Ile Asp Gly Ala Gly Leu
1               5                   10                  15

Gly Phe Asp Val Leu Lys Thr Val Leu Glu Ala Leu Gly Asn Val Lys
            20                  25                  30

Arg Lys Ile Ala Val Gly Ile Asp Asn Glu Ser Gly Lys Thr Trp Thr
        35                  40                  45

Ala Met Asn Thr Tyr Phe Arg Ser Gly Thr Ser Asp Ile Val Leu Pro
    50                  55                  60

His Lys Val Ala His Gly Lys Ala Leu Leu Tyr Asn Gly Gln Lys Asn
65                  70                  75                  80

Arg Gly Pro Val Ala Thr Gly Val Val Gly Val Ile Ala Tyr Ser Met
                85                  90                  95

Ser Asp Gly Asn Thr Leu Ala Val Leu Phe Ser Val Pro Tyr Asp Tyr
            100                 105                 110

Asn Trp Tyr Ser Asn Trp Trp Asn Val Arg Val Tyr Lys Gly Gln Lys
        115                 120                 125

Arg Ala Asp Gln Arg Met Tyr Glu Glu Leu Tyr Tyr His Arg Ser Pro
    130                 135                 140

Phe Arg Gly Asp Asn Gly Trp His Ser Arg Gly Leu Gly Tyr Gly Leu
145                 150                 155                 160

Lys Ser Arg Gly Phe Met Asn Ser Ser Gly His Ala Ile Leu Glu Ile
                165                 170                 175

His Val Thr Lys Ala Gly Ser Ala His His His His His His
            180                 185                 190


<210> SEQ ID NO 14
<211> LENGTH: 21
<212> TYPE: PRT
<213> ORGANISM: Artificial Sequence
<220> FEATURE:
<223> OTHER INFORMATION: endothelin 1

<400> SEQUENCE: 14

Cys Ser Cys Ser Ser Leu Met Asp Lys Glu Cys Val Tyr Phe Cys His
```

-continued

```
1               5                   10                  15

Leu Asp Ile Ile Trp
            20


<210> SEQ ID NO 15
<211> LENGTH: 21
<212> TYPE: PRT
<213> ORGANISM: Artificial Sequence
<220> FEATURE:
<223> OTHER INFORMATION: endothelin-2

<400> SEQUENCE: 15

Cys Ser Cys Ser Ser Trp Leu Asp Lys Glu Cys Val Tyr Phe Cys His
1               5                   10                  15

Leu Asp Ile Ile Trp
            20
```

BIOLOGICAL NANOPORES FOR BIOPOLYMER SENSING AND SEQUENCING BASED ON FRAC ACTINOPORIN

RELATED APPLICATIONS

This application is a continuation of U.S. patent application Ser. No. 16/317,119, filed Jan. 11, 2019, which is a National Stage Application under 35 U.S.C. 371 of expired PCT application PCT/NL2017/050331 designating the United States and filed May 24, 2017; which claims the benefit of U.S. provisional application No. 62/360,999 and filed Jul. 12, 2016 each of which are hereby incorporated by reference in their entireties.

SEQUENCE LISTING

The instant application contains a Sequence Listing which has been submitted electronically in ASCII format and is hereby incorporated by reference in its entirety. Said ASCII copy, created on Apr. 11, 2022, is named "Sequence Listing 005032.00414.txt" and is 9651 bytes in size.

The invention relates generally to the field of nanopores and the use thereof in various applications, such as analysis of biopolymers and macromolecules, typically by making electrical measurements during translocation through a nanopores.

Nanopores represent an attractive way to analyse biopolymers, for example to determine the identity of a polypeptide or polynucleotide, or to estimate the identity of individual building blocks in the polymer for sequencing purposes. This is because the method is label-free, provides measurements dependent on small numbers or even single molecules, and generates an electric signal that is highly scalable.

In a measurement system utilising a nanopore, some property of the system depends on the nucleotides in the nanopore, and electrical measurements of that property are taken. For example, a measurement system be created by placing a nanopore in an insulating membrane and measuring voltage-driven ion flow through the nanopore in the presence of nucleotides of the polynucleotide.

Nanopores have emerged as a powerful approach for single-molecule monitoring of chemical and enzymatic reactions, detection of proteins and sequencing of nucleic acids.[1],[2]. Phi29[3] as well as ClyA[4] have been shown to allow translocation of double stranded DNA. Recently, aerolysin was used to discriminate homopolymers consisting of adenine but differing in length.[5] To date, only αHL and MspA have been shown to discriminate nucleic acids. Both nanopores have β-sheets in their transmembrane region. When DNA is threaded through MspA, the current blocked levels are affected by four or more nucleotides[6] while αHL has three sensing zones in its barrel-shape structure, which accommodates about 20 nucleobases.[7]

The present invention provides novel nanopores with different structures and recognition sites which offer improvements in sequencing accuracy and/or provide different error profiles. Here, we describe the purification and pre-oligomerization of Fragaceatoxin C (FraC), an α-helical pore-forming toxin that is a member from the actinoporin protein family, in complex with sphingomyelin and the reconstitution into planar lipid bilayers composed of 1,2-diphytanoyl-sn-glycero-3-phosphocholine (DPhPC). The present inventors furthermore engineered a FraC mutant (e.g. ReFraC) that permitted capture and translocation of ssDNA and discriminated homopolymers of adenine, thymine and cytosine immobilized with neutravidin (NA). Strikingly, dsDNA could be translocated through FraC, most probably via the elastically deformed α-helical constriction of the nanopore.

Notably, it was found that the FraC nanopore has an ideal shape for protein sequencing and folded protein analysis. It is shown herein below that the electro-osmotic flow is the dominant force that induces the entry of proteins and polypeptides inside the nanopore. By tuning the inner surface of the nanopore, either by precise engineering the constriction of the nanopore or by changing the solution pH, the translocation of both positively and negatively charged polypeptides could be observed. This is remarkable, because it shows that it is possible to induce an electro-osmotic flow that is strong enough to transport both positive and negative residues at a fixed applied potential. It was remarkably found that a series of (unfolded) proteins of different size, e.g. ranging from 1.2-25 kDa, can be distinguished on the basis of individual blockades. Using a 20 amino acid model polypeptide, it is demonstrated that even differences in a single amino acid residue can be observed by nanopore recordings, indicating that FraC nanopores allow the identification of specific sequence features in translocating polypeptides.

Furthermore, the inventors devised a method to reconstitute pre-oligomerized FraC nanopores in sphingomyelin-free planar lipid bilayers. The ReFraC nanopore was engineered to allow electrophoretic DNA capture and showed discrimination among ssDNA homopolymers. In contrast to other nanopores used to sequence DNA (e.g. αHL and MspA), FraC has a α-helical V-shaped transmembrane region which is advantageous to fine-tune nucleobase discrimination. This is because amino acids substitutions at different positions within the transmembrane α-helices may modulate both the size and chemical composition of the constriction.

It is also shown herein that ReFraC induces the unzipping of DNA duplexes at low applied potentials or allows their translocation at high applied potential. The unzipping of DNA hairpins or higher-ordered DNA structures has been investigated using the αHL nanopore.[20],[21] However, the cis vestibule of ReFraC (5.5 nm) is wider than that of αHL (2.6 nm)[13] or MspA (4.8 nm),[22] indicating that FraC can be advantageously employed to study larger higher-order dsDNA structures, such as G-quadruplexes, or folded RNA structures such as tRNAs.

Accordingly, in a first aspect the invention provides a system comprising a funnel-shaped proteinaceous nanopore comprising an α-helical pore-forming toxin that is a member from the actinoporin protein family. More specifically, the α-helical pore-forming toxin is Fragaceatoxin C (FraC), a mutant FraC, a FraC paralog, or a FraC homolog. FraC may be fused, preferably at its C-terminus, to a protein affinity tag, like a His-tag or Strep-tag.

Very good results can be obtained with a mutant FraC. For example, the mutant FraC comprises at least one substitution of a negatively charged amino acid residue in the narrow part of the pore into a neutral or positively charged amino acid residue, and/or at least one substitution of a neutral amino acid residue in the narrow part of the pore into a positively charged amino acid residue. For example, the mutant comprises at least one mutation in the transmembrane helices. Preferably, at least one negatively charged amino acid residue is changed into a positively charged amino acid residue. In a preferred embodiment, the mutant FraC comprises a mutation at position 10, preferably mutation Asp10Arg or Asp10Lys (residue numbering as in crystal structure PDB ID 4TSY). The mutant FraC may further comprise one or more compensatory mutation(s) to recover the hemolytic activity of FraC, preferably wherein said compensatory mutation is present at position 2, 9, 34, 52, 112, 150, 153 and/or 159, and/or preferably at position 159. For example, said compensatory mutation is selected from the group consisting of A2S, I9T, A34V, F52Y, W112L, T1501, G153D, K159E, I171T and any combination thereof. In a specific aspect the mutant FraC (further) comprises a mutation at position 159, preferably Lys159Glu. For example, the FraC double mutant D10R/K159E is used.

The nanopore may be is positioned between a first liquid medium and a second liquid medium, wherein at least one liquid medium comprises an analyte, and wherein the system is operative to detect a property of the analyte.

In one embodiment, the system is operative to translocate the analyte through the tunnel. In another embodiment, the system is operative to detect a property of the analyte comprises subjecting the nanopore to an electric field such that the analyte interacts with the nanopore. The applied potential (which creates the electric field) is necessary to have a current. The current is the output signal. For example, the system is operative to detect a property of the analyte comprises subjecting the nanopore to an electric field such that the analyte electrophoretically and/or electro-osmotically translocates through and/or is trapped in the nanopore. The property may be an electrical, chemical, or physical property of the analyte.

Preferably, the nanopore is comprised in a (planar) lipid bilayer. In a specific aspect, the lipid bilayer comprises or consists of phosphatidylcholine (PC), preferably 1,2-diphytanoyl-sn-glycero-3-phosphocholine.

In a second aspect, the invention provides a method for providing a system according to the invention, comprising the steps of

- providing recombinant monomers of said α-helical pore-forming toxin from the actinoporin protein family;
- contacting said monomers with liposomes to assemble them into oligomers;
- recovering the oligomers from the liposomes; and
- contacting the oligomers with a lipid bilayer, which may contain sphingomyelin, to allow the formation of nanopores.

In a third aspect, the invention provides a method comprising applying an electric field to a system as herein disclosed, wherein the funnel-shaped nanopore comprising an α-helical pore-forming toxin is positioned between a first conductive liquid medium and a second conductive liquid medium. At least one of the conductive liquid media may comprise an analyte. The method may further comprise the step of detecting the analyte in a method comprising measuring an ion current as the analyte interacts with the nanopore to provide a current pattern, wherein the appearance of a blockade in the current pattern indicates the presence of the analyte. The method may further comprise identifying the analyte, for example by comparing the current pattern to a known current pattern obtained using a known analyte under the same conditions. The analyte can be a nucleotide, a nucleic acid, an amino acid, a peptide, a protein, a polymer, a drug, an ion, a pollutant, a nanoscopic object, or a biological warfare agent.

In one embodiment, the analyte is a polymer, such as a protein, a peptide, or a nucleic acid. Preferably, the analyte is a nucleic acid, like ssDNA, dsDNA, RNA, or a combination thereof. In another preferred aspect, the analyte is a protein, a polypeptide or an oligopeptide, e.g. having a size of from about 1 to about 40 kDa, preferably about 1 to about 30 kDa. In one embodiment, the analyte is an oligopeptide (~10 or fewer amino acids), polypeptide (>10 amino acids) or folded protein (>50 amino acids).

In a method of the invention, the FraC nanopore is preferably a mutant FraC nanopore. The conductance through the tunnel of the mutant FraC nanopore is typically higher than the conductance through its corresponding wild-type FraC nanopore.

A still further aspect relates to a mutant Fragaceatoxin C (FraC) nanopore comprising at least a first mutant FraC monomer comprising at least one substitution of a negatively charged amino acid residue in the narrow part of the pore and/or at least one substitution of a neutral amino acid residue in the narrow part of the pore into a positively charged amino acid residue. For example, the mutant comprises at least one mutation in the transmembrane helices. Preferably, at least one negatively charged amino acid residue is changed into a positively charged amino acid residue. The mutant may comprise a substitution at position 3 or position 10, or both positions 3 and 10. In a preferred embodiment, the mutant FraC comprises a mutation at position 10, preferably mutation Asp10Arg or Asp10Lys (residue numbering as in crystal structure PDB ID 4TSY). The mutant FraC may further comprise one or more compensatory mutation(s) to recover the hemolytic activity of FraC, preferably wherein said compensatory mutation is present at position 2, 9, 34, 52, 112, 150, 153 and/or 159, and/or preferably at position 159. For example, said compensatory mutation is selected from the group consisting of A2S, I9T, A34V, F52Y, W112L, T1501, G153D, K159E, I171T and any combination thereof. In a specific aspect the mutant FraC (further) comprises a mutation at position 159, preferably Lys159Glu. Very good results can be obtained with the FraC double mutant D10R/K159E. Specifically preferred mutants include those of Table 3 herein below.

The mutant FraC nanopore may further comprise at least a second monomer selected from the group consisting of a wild-type FraC monomer, a second mutant FraC monomer, a wild-type FraC paralog or homolog monomer, and a mutant FraC paralog or homolog monomer, wherein the second mutant FraC monomer may be the same or different than the first mutant FraC monomer. For example, the second monomer is a wild-type FraC paralog or homolog monomer. In one embodiment, the first mutant FraC monomer of the mutant FraC nanopore comprises mutation DIOR, preferably wherein the mutant is selected from those depicted in Table 3.

The mutant FraC nanopore preferably has a conductance through the tunnel that is higher than the conductance through the tunnel of its corresponding wild-type FraC nanopore.

The mutant FraC nanopore may further comprise a molecular motor, wherein the molecular motor is capable of moving an analyte into or through the nanopore with an average translocation velocity that is less than the average translocation velocity at which the analyte translocates into or through the nanopore in the absence of the molecular motor.

For example, the molecular motor is an enzyme, like a polymerase, an exonuclease, or a Klenow fragment.

For protein analysis, it is preferred to have an electroosmotic flow (EOF), from the cis to trans compartment, which is induced by a charged constriction. The translocation of amino acids of the same charge as the constriction can be obtained by manipulation of the pH of the analyte solution. It is advantageous to use one or more unnatural amino acids that maintain a negative charge at low pH values (<~4.5), for example sulfate ($SO_4^{2-}$), or phosphate ($PO_4^{2-}$) moieties are suitable amino acid side chain groups. Hence, also provided is a nanopore that is engineered to have a strong electroosmotic flow from the cis to trans compartment under negative applied potential (pH 4.5 or lower).

The invention also provides the use of a system as herein disclosed, or a mutant FraC nanopore according to the invention, for biopolymer sensing and/or biopolymer sequencing. For example, said biopolymer is a protein, a peptide, or a nucleic acid. Preferably, provided is the use of a system as herein disclosed, or a mutant FraC nanopore according to the invention, for sensing and/or sequencing of a nucleic acid, like ssDNA, dsDNA, RNA, or protein or polypeptide, or a combination thereof.

For example, a FraC nanopore is advantageously used to recognize protein, polypeptide and oligopeptide biomarkers. Once inside the nanopore proteins and polypeptides of different sizes can be distinguished by ionic currents. Although individual amino acids could not be identified on-the-fly during translocation, we showed that two small (unfolded) oligopeptides endothelin 1 and endothelin 2 (2.5 kDa), which differ by just one tryptophan residue could be differentiated by ionic current recordings. Therefore, if the translocation of a polypeptide can be controlled e.g. by the use of enzymes, FraC nanopores allow for the identification of specific sequence features in translocating polypeptides.

In one embodiment, a (mutant) FraC nanopore is used as a sensor in single-molecule proteomic analysis. In the simplest implementation of nanopore proteomics, proteins are recognized amino acid-by-amino acid as they translocate linearly through a nanopore. Since the sequence of proteins and oligopeptides in an organism is known from genomic analysis, proteins might be recognized simply by comparing a specific protein blockade during the unfolded translocation across a nanopore with a database of known protein blockades. Alternatively, folded proteins could be recognized as they lodge inside the nanopore vestibule with or without translocating the nanopore.

LEGEND TO THE FIGURES

The patent or application file contains at least one drawing executed in color. Copies of this patent or patent application publication with color drawing(s) will be provided by the Office upon request and payment of the necessary fee.

FIG. 1. Wild type FraC (WtFraC) and D10R-K159E FraC (ReFraC) nanopores (A) Cross-section through octameric WtFraC showing coulombic surface coloring (red=negative charges, blue=positive charges). Aspartate residue 10, located in the constriction zone of WtFraC, is indicated. (B) Top view on WtFraC (top) and ReFraC (bottom). (C) Single channel conductance histogram for WtFraC (blue) and ReFraC (red) at +50 mV in 1M NaCl, 15 mM Tris.HCl pH 7.5. (D) Raw trace of WtFraC (top) and ReFraC (bottom) at +100 mV in 3 M NaCl, 15 mM Tris.HCl pH 7.5 buffer obtained with identical acquisition settings (2 kHz low-pass Bessel filter and 10 kHz sampling rate).

Figure 2:
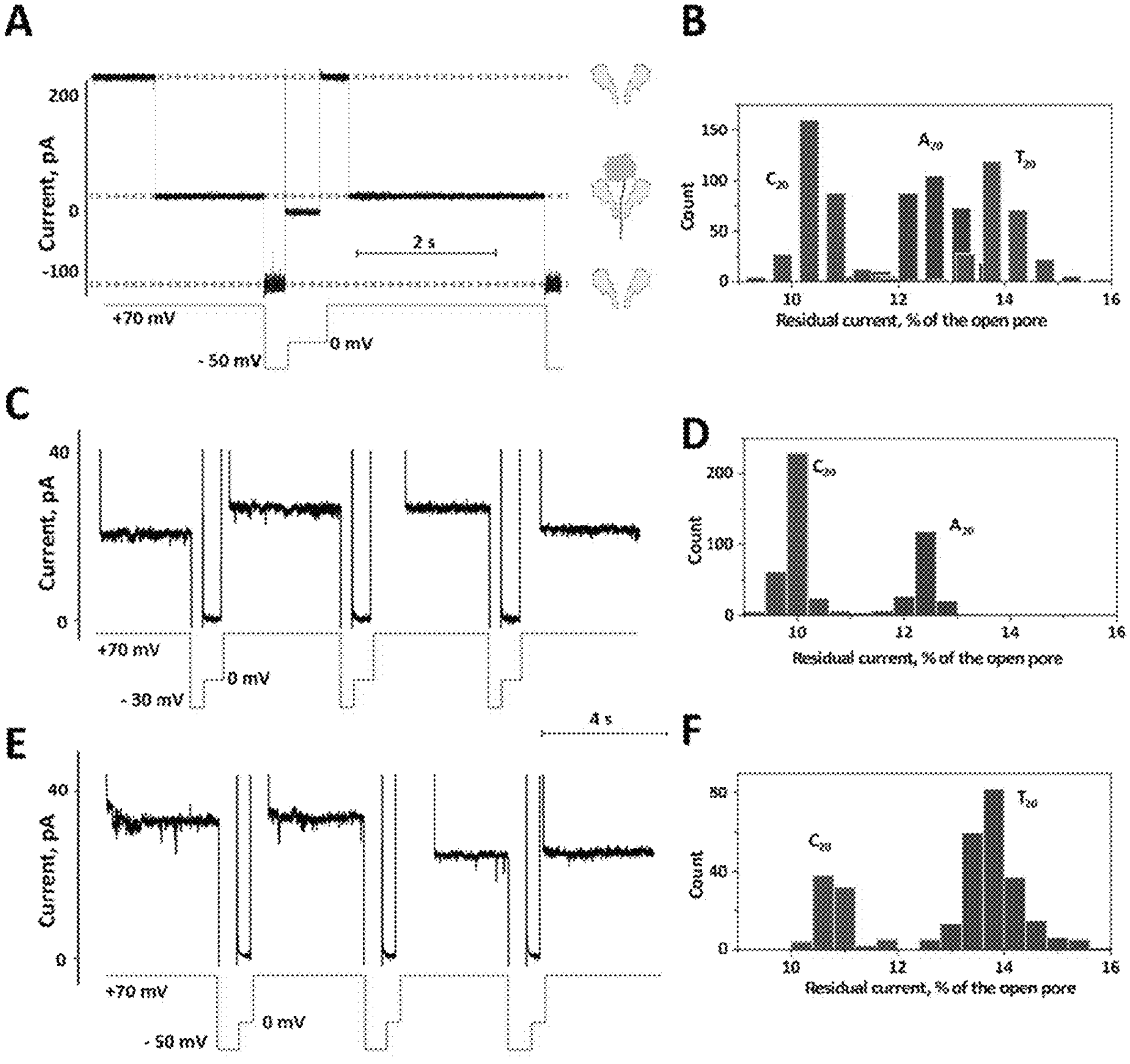

FIG. 2. DNA discrimination with ReFraC (A) Representative blockades of a homopolymeric DNA strand in complex with NA using ReFraC. The cartoon shows the interpretation of the current blockades. (B) Representative distributions of residual currents obtained for $A_{20}$, $C_{20}$, $T_{20}$ homopolymeric strands with ReFraC nanopores (C) Current blockades of a continuous trace induced by homopolymeric $C_{20}$ and $A_{20}$ nucleotides to the same ReFraC pore. Traces shown were digitally filtered with 100 Hz cut-off. (D) Distribution of residual currents imposed by mixtures of $C_{20}$ and $A_{20}$ homopolymeric strands (E) Continuous trace of an experiment to resolve mixtures of homopolymeric $C_{20}$ and $T_{20}$ nucleotides (F) Distribution of residual currents imposed by mixtures of $C_{20}$ and $T_{20}$ homopolymeric strands. Traces were recorded in 3 M NaCl, 15 mM Tris.HCl, pH 7.5, using 2 kHz low-pass Bessel filter and 10 kHz sampling rate. Traces C and E were subjected to additional 100 Hz Gaussian digital filtering.

Figure 3:
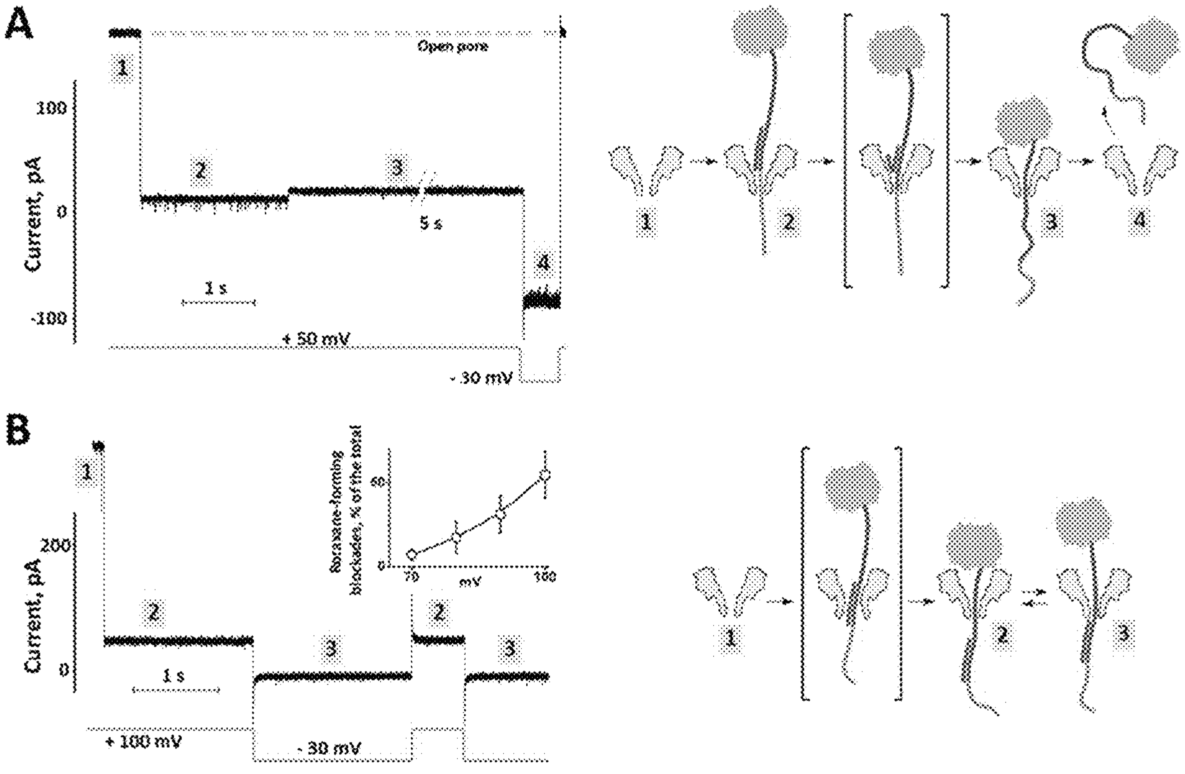

FIG. 3. Unzipping/Translocation of dsDNA by ReFraC (A) Representative trace of ReFraC capturing a NA:A (dsDNA)C complex at +50 mV. The open pore current is denoted as "1" and for comparison indicated after capture of the complex. Two levels can be observed in the block: firstly, a lower level ("2"), likely corresponding to homopolymeric cytosine which converts via an intermediate level (unzipping, brackets) into a higher level ("3"), most likely corresponding to homopolymeric adenine. Upon reversal of potential ("4") the block is immediately released indicating that the double-stranded region NA:A(dsDNA)C complex was peeled off. (B) At+100 mV, in more than half of the cases (insert) a single block ("2") is observed after the dsDNA part is pushed through (deformation, brackets) and upon application of −30 mV the block cannot be released immediately ("3"). At higher negative potentials the block can be released, indicating a rotaxane was formed (more examples in FIG. 8). Traces were recorded in 3 M NaCl, 15 mM Tris.HCl, pH 7.5, using 2 kHz low-pass Bessel filter and 10 kHz sampling rate.

Figure 4:
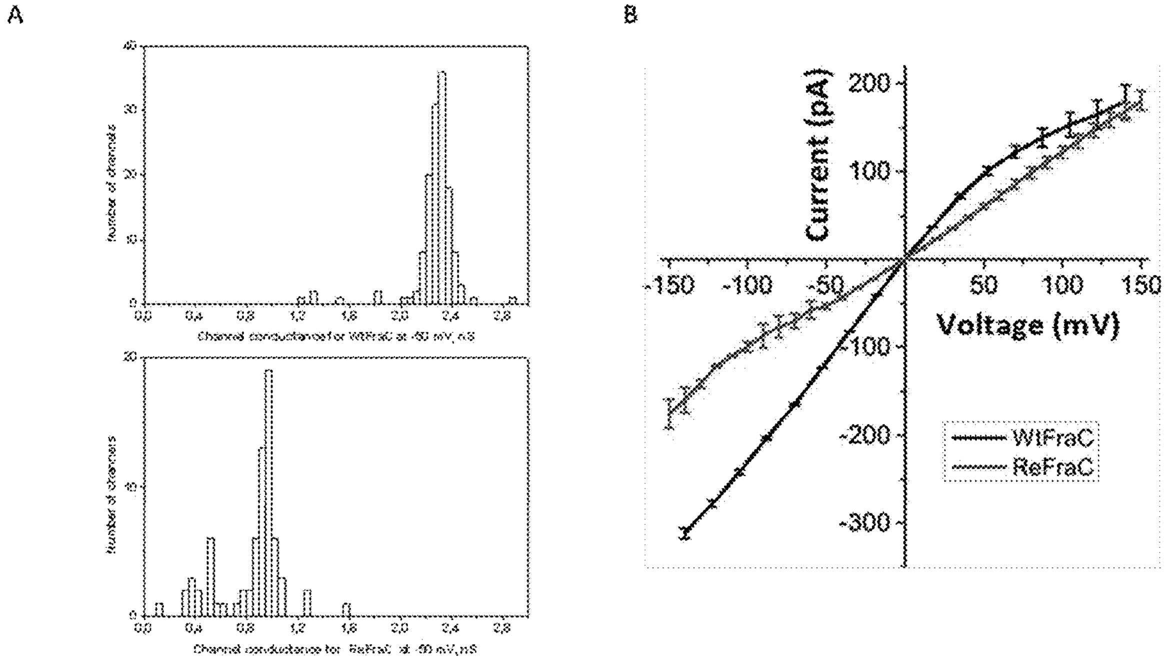

FIG. 4. Unitary channel conductance distribution and voltage current dependence determined for WtFraC and ReFraC nanopores. A: Unitary channel conductance distribution measured for WtFraC (top) and ReFraC (bottom) pre-oligomerized pores reconstituted in planar lipid bilayers. The conductance was measured at −50 mV applied potential. The orientation of each individual channel was verified according to the asymmetry in conductance. B: Voltage current dependence measured for WtFraC and ReFraC nanopores. Experiments were repeated 3 times, and error bars indicate the standard deviations between experimental values. Recordings were carried out in 15 mM Tris.HCl pH 7.5 and 1M NaCl.

Figure 5:
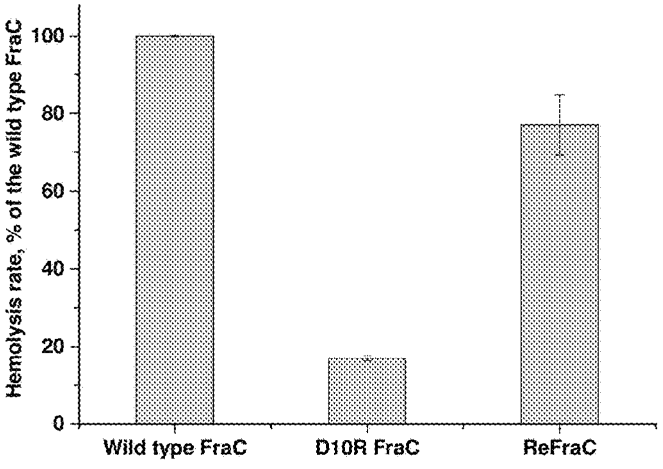

FIG. 5. Hemolytic activity of the WtFraC, D10R FraC and ReFraC. Hemolysis rate was calculated as inverse of the time elapsed till 50% decrease in turbidity (measured as optical density at 650 nm wavelength) observed in 1% of horse erythrocytes suspension in 15 mM Tris.HCl pH 7.5 150 mM NaCl. Proteins were added in 200 nM concentration, hemolysis rates are presented as percentage of WtFraC. Experiment was repeated 3 times, and error bars indicate the standard deviation between experimental values.

Figure 6:
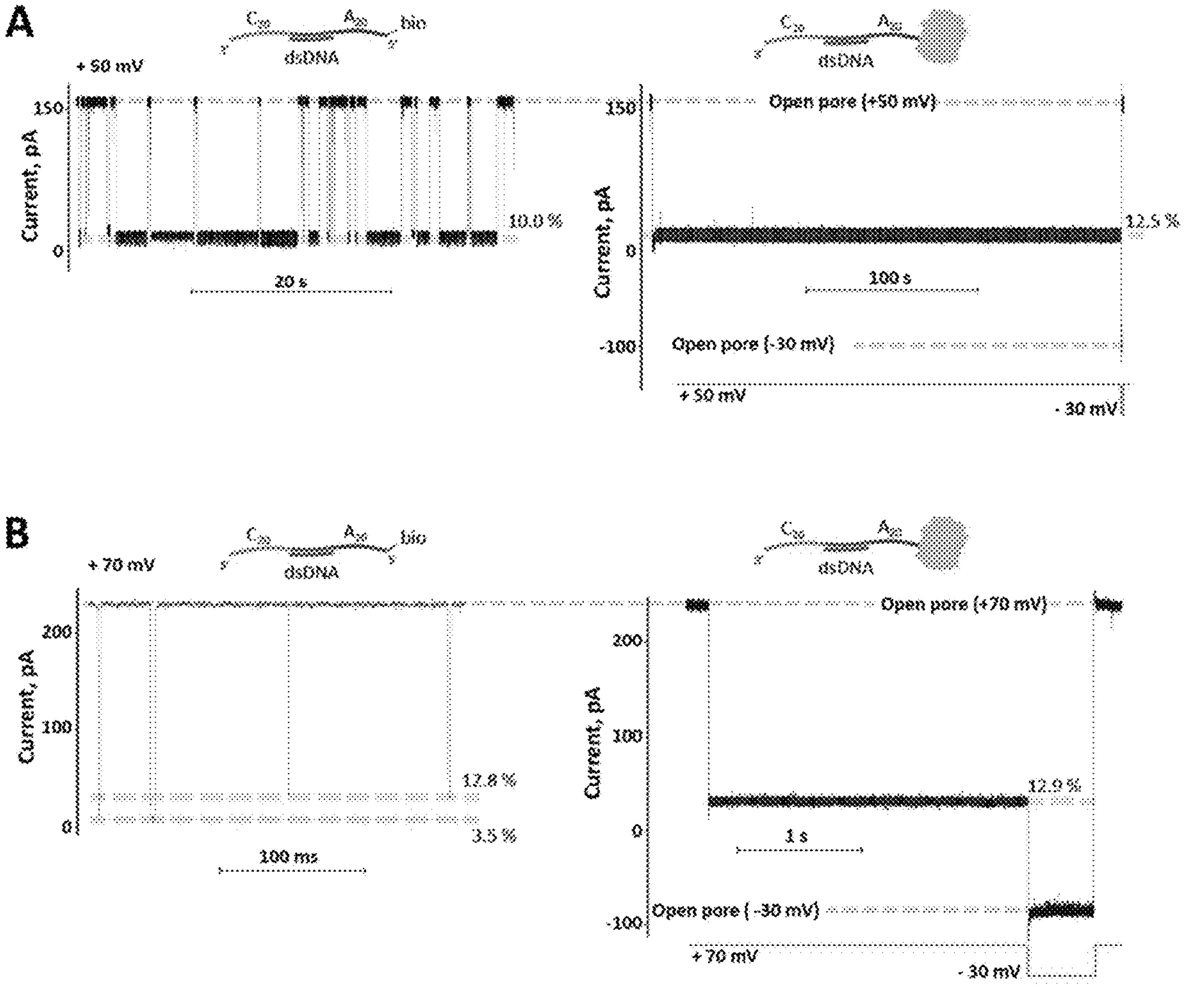

FIG. 6. Translocation and immobilization of A(dsDNA)C DNA substrate recorded with ReFraC nanopore.

A(dsDNA)C substrate (depicted above the trace) was made by annealing of oligo I

SEQ ID NO: 1

(5' biotinylated AAAAAAAAAAAAAAAAAAAAGTGCTACGACTCT CTGTGTGCCCCCCCCCCCCCCCCCCCC)

and oligo II (CACACA GAGAGTCGTAGCAC) SEQ ID NO:2. A: Blockades provoked on ReFraC nanopore by 1 μM of A(dsDNA)C alone (left) and in complex with 0.25 μM of neutravidin (right), substrates were added in cis under +50 mV applied potential. B: Blockades provoked on ReFraC nanopore by 1 μM of A(dsDNA)C alone (left) and in complex with 0.25 μM of neutravidin (right), substrates were added in cis under at +70 mV. Two levels of the residual current detected for free A(dsDNA)C blockades indicated with pale violet dashed line. Current levels corresponding to the blocked and open pores are shown as pale violet and grey dashed lines respectively. Voltage stepping protocols are shown with the red lines below the traces. Recordings were carried out in 15 mM Tris.HCl pH 7.5 and 3M NaCl, sampling frequency was 10 kHz, and data were smoothed by 2 kHz low-pass Bessel filter upon acquisition.

Figure 7:
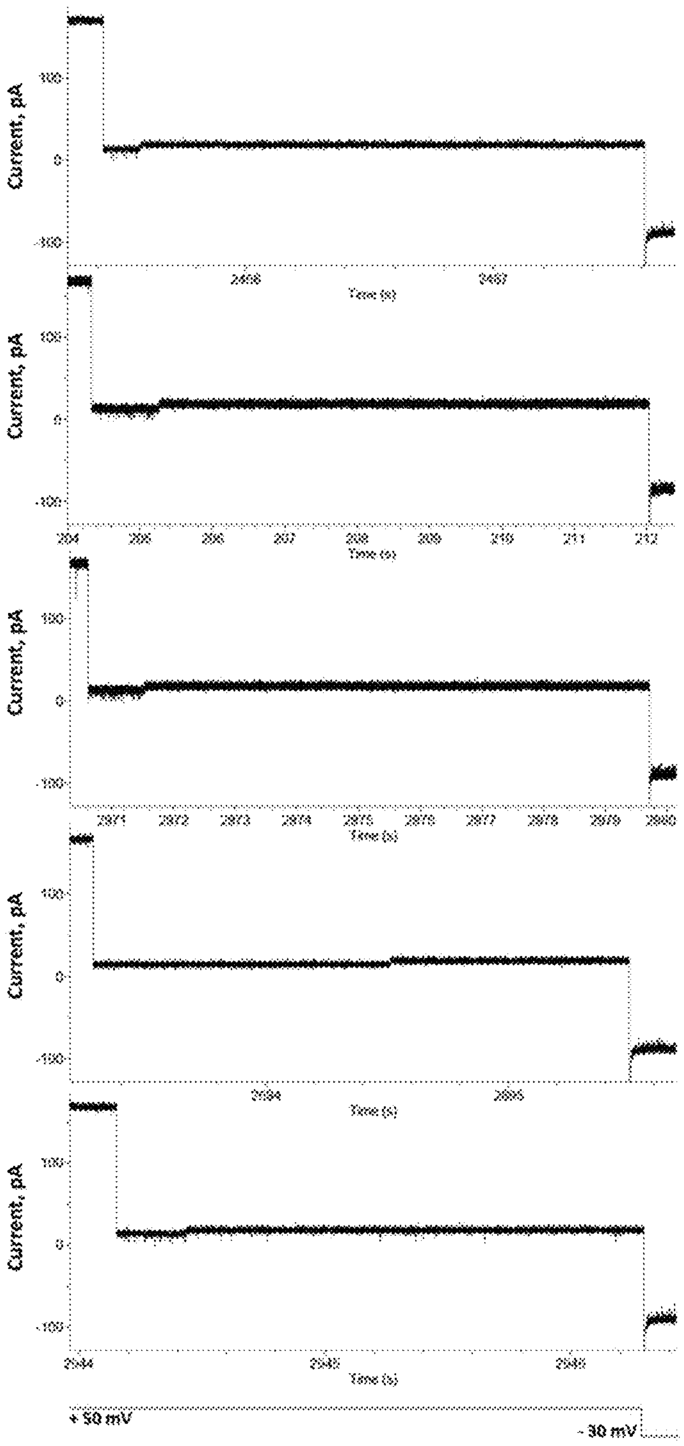

FIG. 7. Representative traces showing stepwise enhancements of the residual current within A(dsDNA)C-neutravidin blockades provoked on ReFraC nanopore. 1 μM of A(dsDNA)C and 0.25 μM of neutravidin were present in cis at +50 mV. Within the blockades residual current has switched from 8.8±0.7% (initial level) to 12.5±0.7% (final level). Voltage stepping protocol is shown with the red lines at the bottom. Recordings were carried out in 15 mM Tris.HCl pH 7.5 and 3M NaCl, sampling frequency was 10 kHz, and data were smoothed by 2 kHz low-pass Bessel filter upon acquisition.

Figure 8:
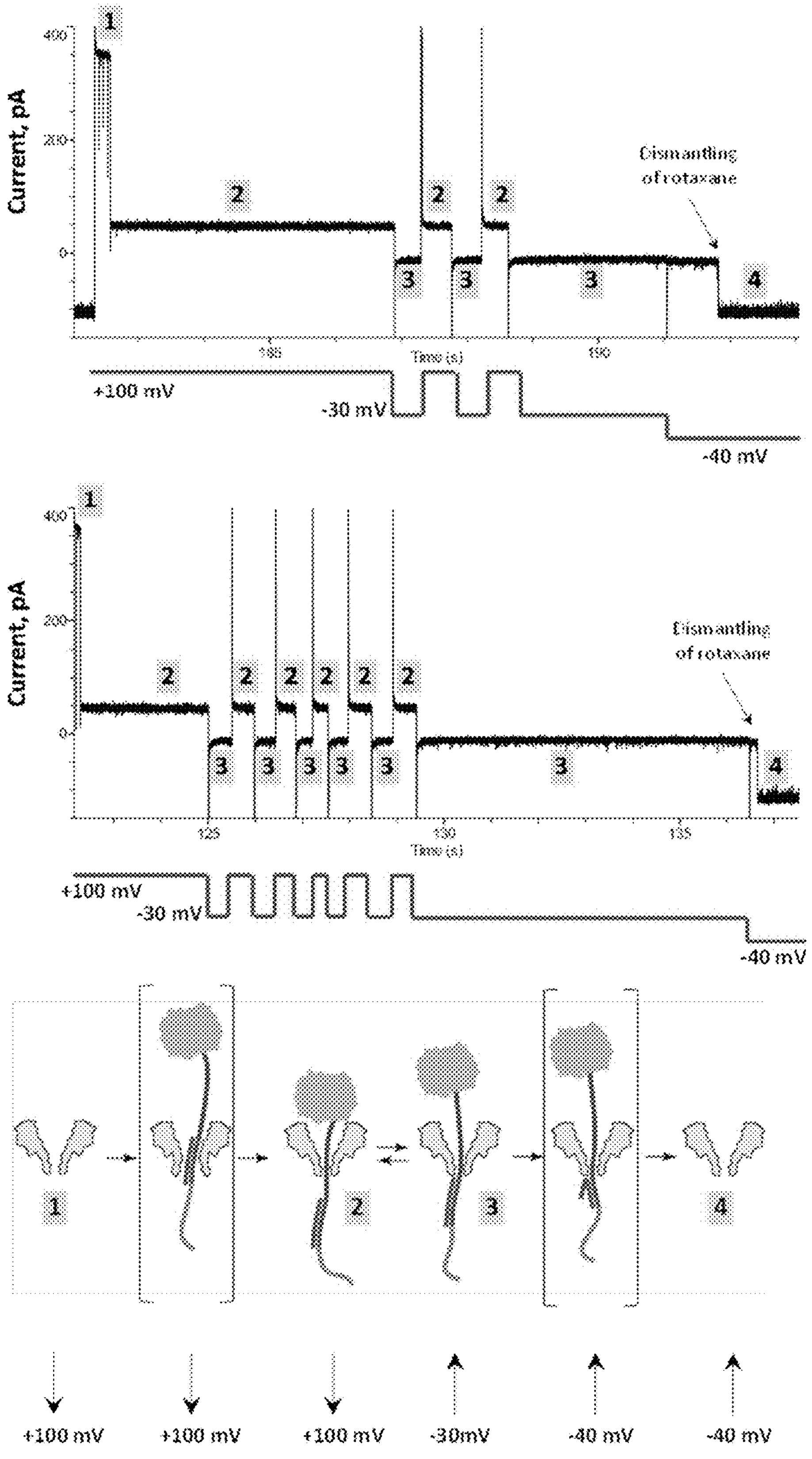

FIG. 8. Additional examples of traces showing rotaxane formation by A(dsDNA)C-neutravidin driven into ReFraC nanopore at +100 mV applied potential. 1 μM of A(dsDNA)C and 0.25 μM of neutravidin were added in cis. Voltage stepping protocols are shown with the red lines at the bottom. Rotaxanes were dismantled by switching the applied potential to −40 mV. Recordings were carried out in 15 mM Tris.HCl pH 7.5 and 3M NaCl, sampling frequency was 10 kHz, and data were smoothed by 2 kHz low-pass Bessel filter upon acquisition.

Figure 9:
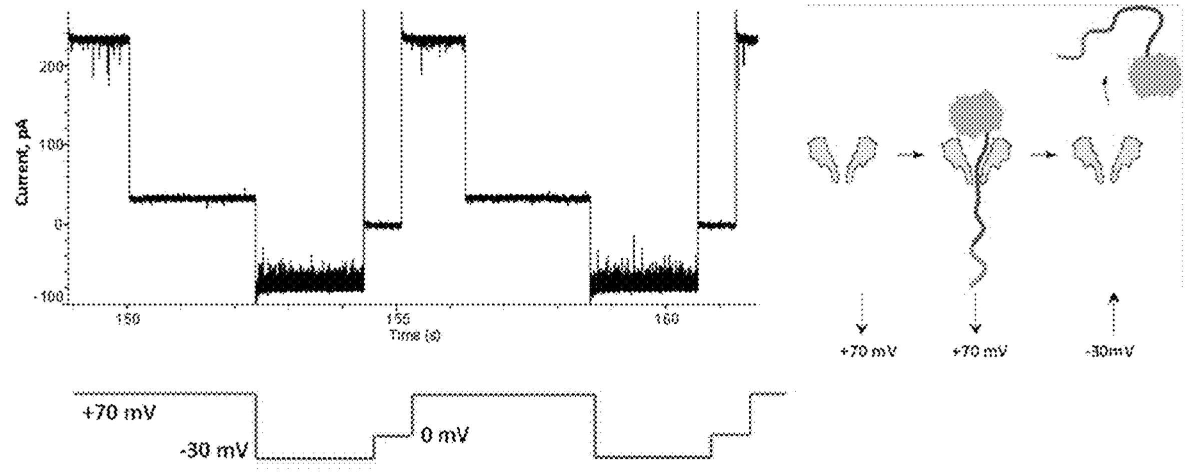
Figure 9:
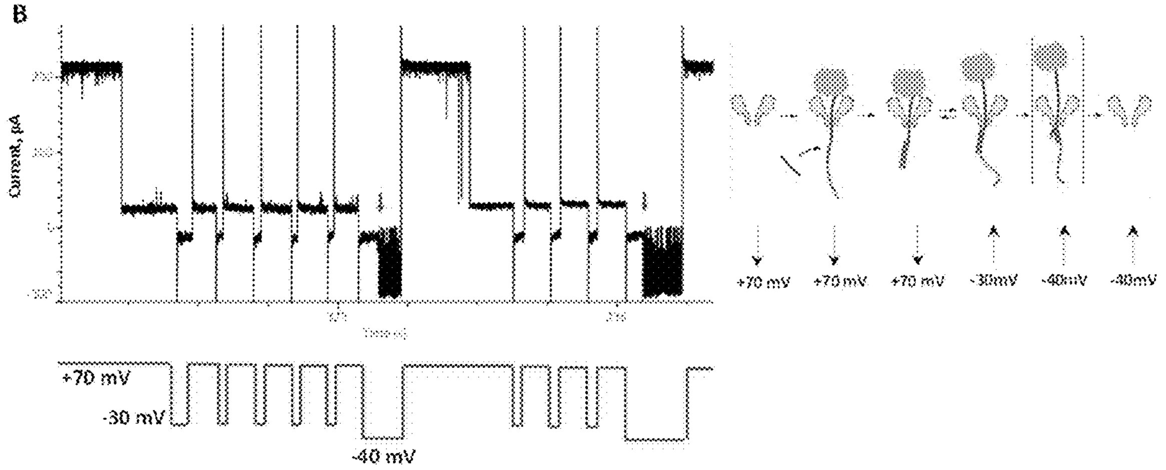

FIG. 9: Representative traces showing pseudorotaxane and rotaxane formation by oligonucleotide I—neutravidin immobilized within the ReFraC nanopore. A: Pseudorotaxane formation provoked by 1 μM of oligo I and 0.25 μM of neutravidin present in cis. B: Rotaxane formation by 1 μM of oligonucleotide I and 0.25 μM neutravidin present in cis while 1 μM of oligonucleotide II was added in trans. Rotaxanes were dismantled by switching the applied potential to −40 mV (red arrow above the trace indicates the dismantling of rotaxane). Transient state describing unzipping of dsDNA is shown in brackets. Voltage stepping protocol is shown with the red lines at the bottom. Recordings were carried out in 15 mM Tris.HCl pH 7.5 and 3M NaCl, sampling frequency was 10 kHz, and data were smoothed by 2 kHz low-pass Bessel filter upon acquisition.

Figure 10:
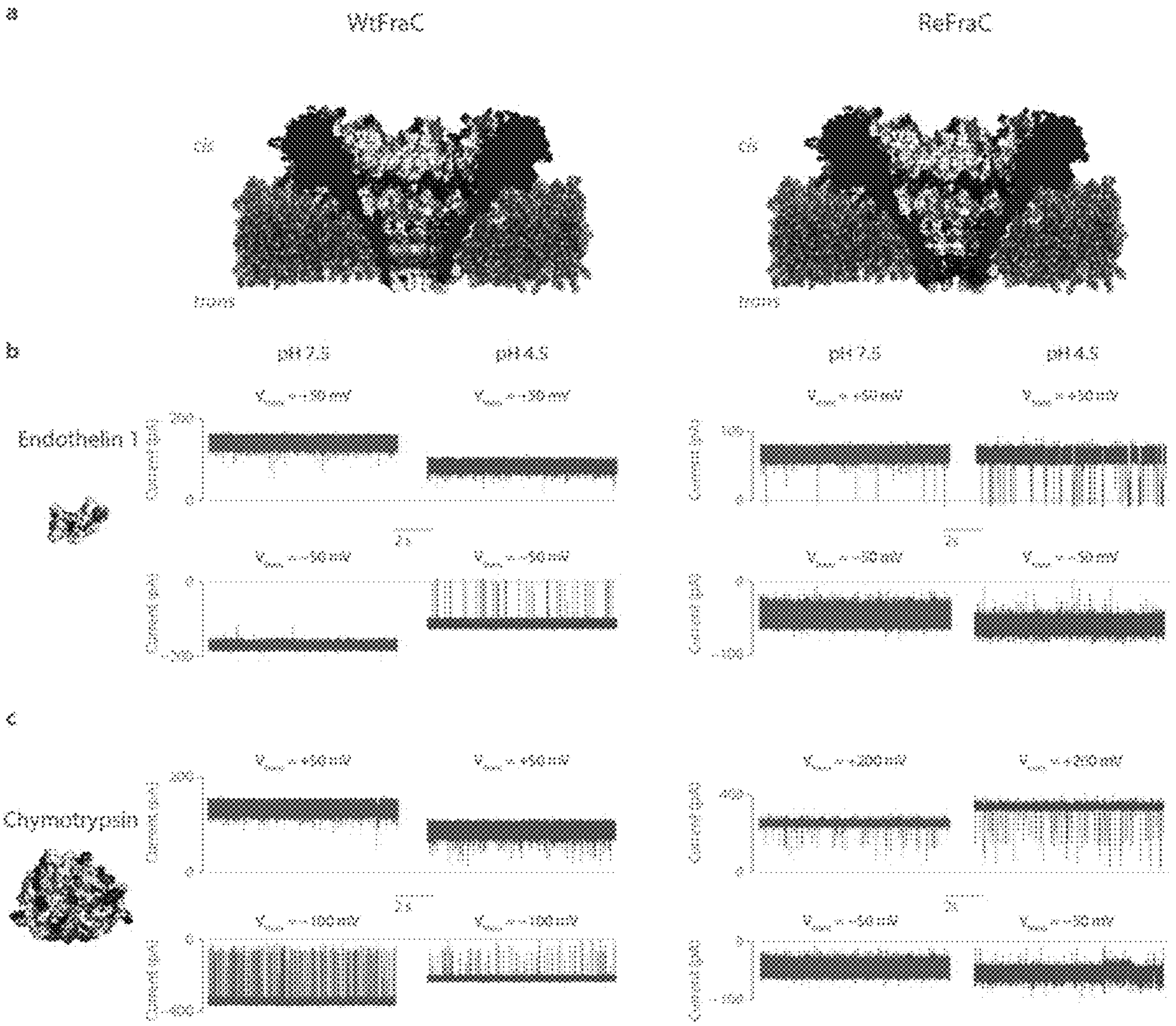

FIG. 10. Capture of an oligopeptide (Endothelin 1) and a protein (Chymotrypsin) with two FraC variants at two different pH conditions. a) Cross sections of wild type FraC (WtFraC, PDB: 4TSY) and D10R-K159E-FraC (ReFraC). b-c) Representative traces induced by 1 μM endothelin 1 (b) and 200 nM chymotrypsin (c) to WtFraC (left) and ReFraC (right). Chymotrypsin (PDB: 5CHA) and human endothelin 1 (PDB: 1EDN) are shown as surface representations. Endothelin 1 and chymotrypsin enter WtFraC under negative applied potentials, while they enter ReFraC under positive applied potentials. Chymotrypsin blockades to WtFraC were also observed under −50 mV at pH 7.5 and 4.5, however, the applied potential was increased to −100 mV to obtain a sufficient number of blockades. At pH 7.5, blockades to ReFraC by chymotrypsin under positive applied bias required higher potential than to WtFraC under negative applied bias. The buffer at pH 7.5 included 1 M KCl, 15 mM Tris, and the buffer at pH 4.5 contained 1 M KCl, 0.1 M citric acid, 180 mM Tris.Base. Endothelin 1 and chymotrypsin were added into cis compartment. All traces were recorded using 50 kHz sampling rate and a 10 kHz low-pass Bessel filter. The coloring represents the electrostatic potential of the molecular surface as calculated by APBS(13) (pH 7.5 in 1 M KCl) with red and blue corresponding to negative and positive potentials (range −4 to +4 kbT/ec), respectively. Structures were rendered using PyMOL.

Figure 11:
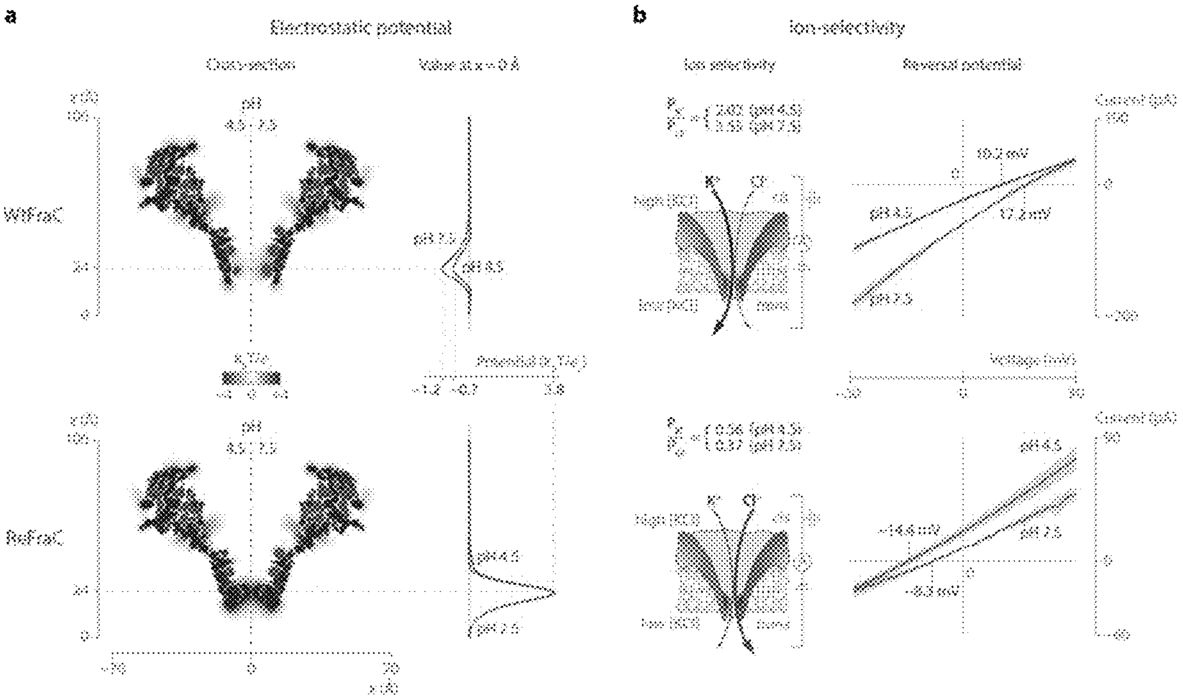

FIG. 11. Electrostatic distribution and ion-selectivity of WtFraC and ReFraC. a) The monomer averaged simulated electrostatic potentials reveal the negatively and positively charged constrictions of WtFraC and ReFrac, respectively. While for ReFrac lowering of the pH from 7.5 to 4.5 only had a small effect on the electrostatic potential, for WtFraC the peak value at the center of the constriction dropped ~41%. All simulations were performed using APBS(13) at 1M KCl, with the partial charge of each titratable residue adjusted according to their average protonation states with a modified version of the PDB2PQR software.(14) Residue pKa values were estimated using PROPKA.(33, 34) b) Determination of the reversal potential shows that WtFraC and ReFrac are respectively cation- and anion-selective, as expected from the electrostatic potentials at their constrictions. Lowering the pH from 7.5 to 4.5, reduced the ion selectivity of WtFraC (P_(K^+)/P_([(Cl)]^−)) by ~43%, in accordance with the reduced magnitude of the simulated electrostatic potential. By contrast, the ~37% increase in ion selectivity of ReFraC at pH 4.5 was not predicted by the simulations. All reversal potentials were measured under asymmetric salt conditions (467 mM KCl in trans and 1960 mM KCl in cis) and the ion selectivity determined using the Goldman-Hodgkin-Katz equation. Detailed experiment procedures are given in supporting information. The envelopes behind every current-voltage curve represent their respective standard deviations.

Figure 12:
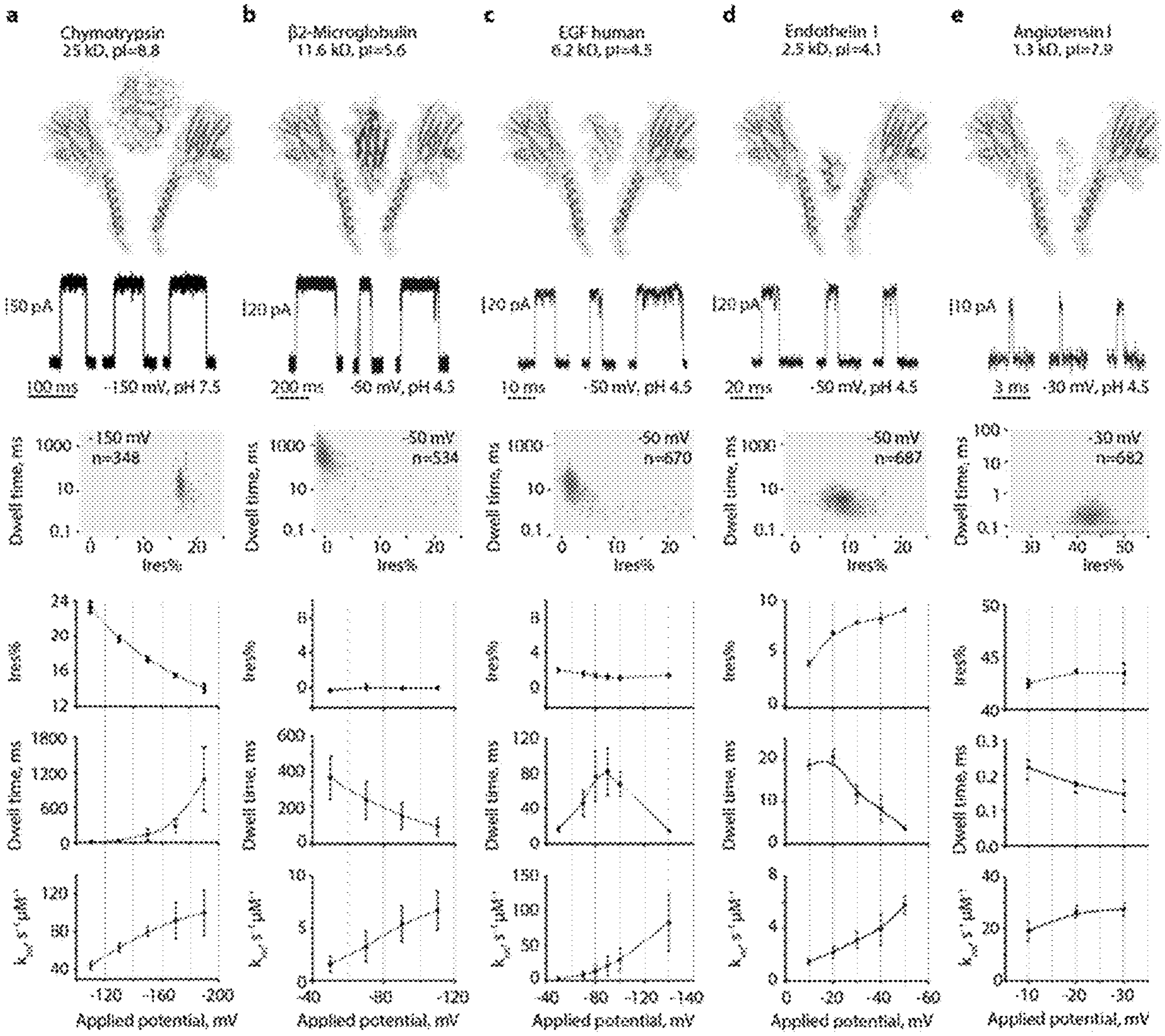

FIG. 12. Biomarker characterization with WtFraC at pH 4.5. a) From top to bottom: surface representation with molecular surface and cartoon representations (Pymol) of chymotrypsin (25 kD, PDB: 5CHA), a representative trace obtained under −150 mV applied potential, a heatplot depicting the dwell time distribution versus Ires % at −150 mV, the voltage dependence of Ires %, the voltage dependence of the dwell times, and the capture frequency. b), c), d), e) show the same information for β2-microglobulin (11.6 kD, PDB: 1LDS), human EGF (6.2 kD, PDB: 1JL9), endothelin 1 (2.5 kD, PDB: 1EDN) and angiotensin I (1.3 kD), respectively. Angiotensin I is depicted as a random structure drawn with Pymol. The concentrations of the biomarkers were: 200 nM for chymotrypsin, 200 nM for β2-microglobin, 2 μM for human EGF, 1 μM for endothelin 1, and 2 μM for angiotensin I, respectively. Isoelectric points of biomarkers are obtained from literatures or with the on line calculation tool Pepcalc. Error bars represent the standard deviation obtained from at least 3 repeats and at least 300 events for each repeat. Data were fitted using a B-spline function (Origin 8.1). All recordings were collected with 50 kHz sampling rate and 10 kHz low-pass Bessel filter.

Figure 13:
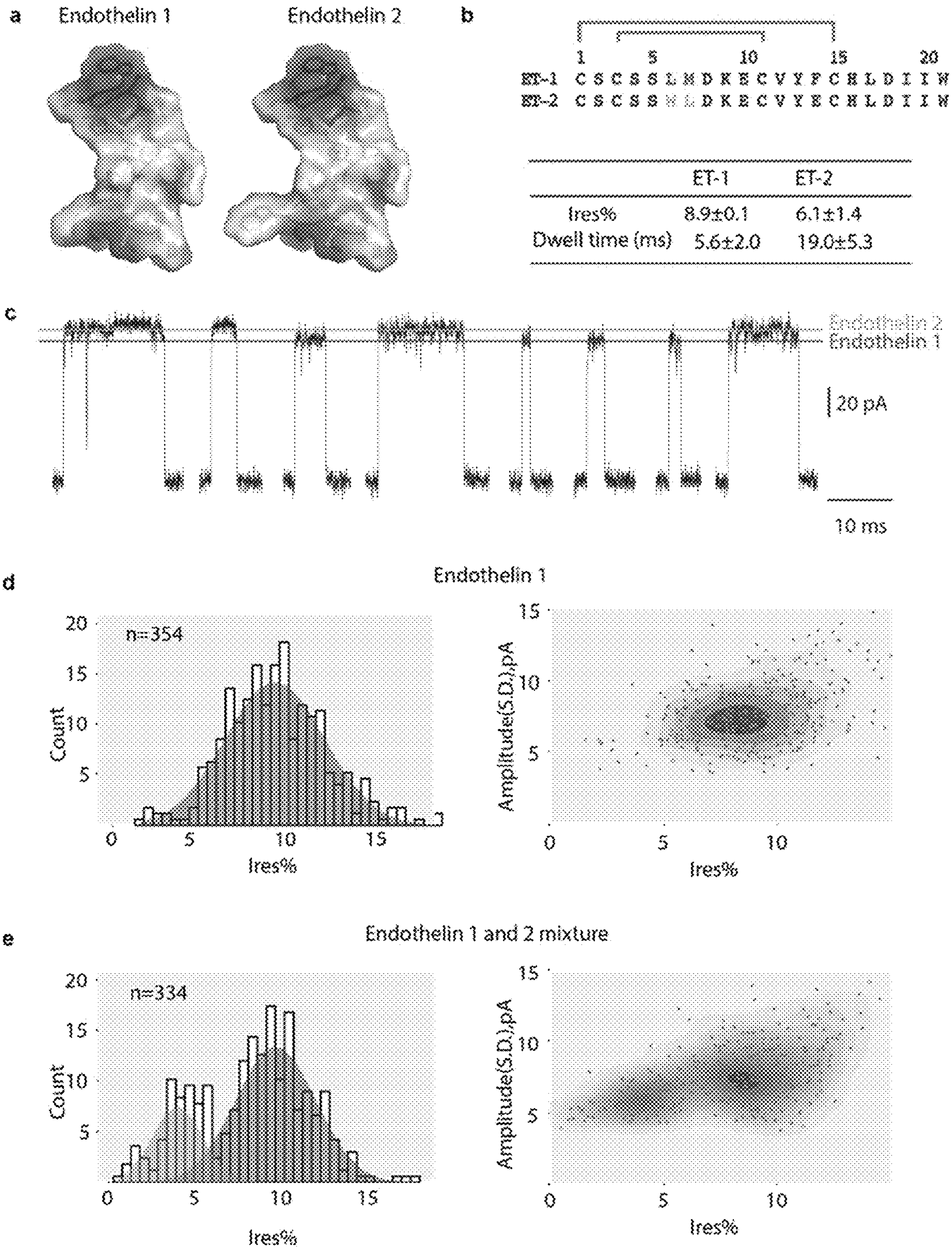

FIG. 13. Discrimination of endothelin 1 SEQ ID NO:14 and 2 SEQ ID NO:15 with WtFraC at pH 4.5. a) Molecular surface representation of endothelin 1 and endothelin 2 using electrostatic coloring (PyMOL). b) Above: amino acid sequences of endothelin 1 and 2. Blue lines indicate the disulfide bridges in each oligopeptide. Below: Ires % and dwell time for endothelin 1 and endothelin 2 blockades at −50 mV in pH 4.5 buffer (1 M KCl, 0.1 M citric acid, 180 mM Tris.Base). c) Representative endothelin 1 and endothelin 2 blockades to the same FraC nanopore under −50 mV applied potential. d) Histogram (left) of residual currents provoked by 2 μM endothelin 1 and corresponding heatplot depicting the standard deviation of the current amplitude versus Ires % (right). e) Same as in (d) but after addition of 8 μM endothelin 2 to the same pore revealing a second population. Graphs were created with custom R scripts. All recordings were conducted with 50 kHz sampling rate and 10 kHz Bessel low-pass filter.

EXPERIMENTAL SECTION

Section A

Materials and Methods

Unless otherwise specified, all chemicals were bought from Sigma-Aldrich. DNA was purchased from Integrated DNA Technologies (IDT). Enzymes were acquired from Fermentas and lipids from Avanti Polar Lipids. All errors in this work are given as standard deviations.

FraC Cloning

To allow cloning, a Nco I restriction site (CCATGG) was introduced at the beginning of the DNA sequence (5' end) corresponding to mature WtFraC from *A. fragacea* SEQ ID NO:13. To maintain the reading frame an additional two bases were inserted after the Nco I site, resulting in an additional alanine residue after the starting methionine. For purification purposes, at the C-terminus of FraC, a His9 affinity tagwas attached via a flexible glycine-serine-alanine linker and the open reading frame was terminated by two consecutive stop codons, followed by a Hind III restriction site (3' end). 50 ng of the synthetic gene with optimized codon composition (IDT) served as a template for the following PCR reaction: the gene was amplified by Phire Hot Start II DNA polymerase (Finnzymes) using 6 μM of primers Frf and Frr (Table 2) in 300 μL volume. The PCR protocol was as follows: a pre-incubation step at 98° C. for 30 s was followed by 30 cycles of denaturation at 98° C. for 5 s and extension at 72° C. for 1 min. The resulting PCR product containing the Hi9-tagged WtFraC gene was purified with QIAquick PCR Purification Kit (Qiagen) and digested with Nco I and Hind III (FastDigest, Fermentas). The gel purified insert (QIAquick Gel Extraction Kit, Qiagen) was cloned under control of the T7 promoter into the pT7-SC1 expression plasmid using sticky-end ligation (T4 ligase, Fermentas) via Nco I (5') and Hind III (3') sites. Of the ligation mixture 0.6 μL was transformed into 50 μL of E. cloni® 10G cells (Lucigen) by electroporation. The transformed bacteria were grown overnight at 37° C. on ampicillin (100 μg/ml) LB agar plates. The identity of the clones was confirmed by sequencing.

Construction of 10R FraC

Of the pT7-SC1 plasmid containing the WtFraC gene 100 ng served as a template for PCR reaction: the gene was amplified by Phire Hot Start II DNA polymerase (Finnzymes) using 6 μM of primers 10Rf (encoding for DIOR) and T7 terminator (Table 2) in a 300 μL volume. The PCR reaction cycling protocol was as follows: a pre-incubation step at 98° C. for 30 s was followed by 30 cycles of denaturation at 98° C. for 5 s and extension at 72° C. for 1 min. The PCR product was gel purified (QIAquick Gel Extraction Kit, Qiagen) and cloned into a pT7 expression plasmid (pT7-SC1) by MEGAWHOP procedure[1]: about 500 ng of the purified PCR product was mixed with about 300 ng of the pT7-SC1 plasmid containing WtFraC gene and the amplification was carried out with Phire Hot Start II DNA polymerase (Finnzymes) in 50 μL final volume (pre-incubation at 98° C. for 30 s, then 30 cycles of: denaturation at 98° C. for 5 s, extension at 72° C. for 1.5 min). The circular template was eliminated by incubation with Dpn I (1 FDU) for 2 hr at 37° C. Of the resulting mixture 0.6 μL was transformed into E. cloni® 10G cells (Lucigen) by electroporation. The transformed bacteria were grown overnight at 37° C. on ampicillin (100 μg/ml) containing LB agar plates. The identity of the clones was confirmed by sequencing.

Construction of 10R FraC Libraries by Error-Prone PCR

Libraries were constructed by amplifying the D10R FraC gene from plasmid DNA using T7 promoter and T7 terminator primers (Table 2).

TABLE 2

Oligonucleotides employed in this study. "5Biosg" stands for biotin group conjugated to 5' end of DNA via C6 linker (IDT).

| Name | DNA sequence |
|---|---|
| Frf | atatatatatccATGGCGAGCGCCGATGTCGCGGGTGCGG SEQ ID NO: 3 |
| Frr | atatatatatAAGCTTATCAGTGATGGTGGTGATGATGCGCAG SEQ ID NO: 4 |
| 10Rf | GCCGATGTCGCGGGTGCGGTAATCcgtGGTGCGGGTCTGGGCTTTGACGTAC SEQ ID NO: 5 |
| Oligo-nucleotide I | /5Biosg/AAAAAAAAAAAAAAAAAAAAGTGCTACGACTCTCTGTGTGCCCCCCCCCCCCCCCCCCCC SEQ ID NO: 1 |
| Oligo-nucleotide II | CACACAGAGAGTCGTAGCAC SEQ ID NO: 2 |
| $A_{20}$ | /5Biosg/ATATATAAAAAAAAAAAAAAAAAAAA SEQ ID NO: 6 |
| $C_{20}$ | /5Biosg/ATATATCCCCCCCCCCCCCCCCCCCC SEQ ID NO: 7 |
| $T_{20}$ | /5Biosg/ATATATTTTTTTTTTTTTTTTTTTTT SEQ ID NO: 8 |
| T7-terminator | GCTAGTTATTGCTCAGCGG SEQ ID NO: 9 |
| T7-promoter | TAATACGACTCACTATAGGG SEQ ID NO: 10 |

In the first round of mutagenesis we used a plasmid containing the synthetic gene encoding for 10R FraC as a template. In the second mutagenesis round we used the pool of DNA plasmids from the clones with highest activity identified in the first round of screening. DNA amplification was performed by error prone PCR: 400 μL of PCR mix (200 μl of REDTaq ReadyMix, 6 μM T7 promoter and T7 terminator primers, ~400 ng of plasmid template) was split into 8 reaction volumes containing from 0 to 0.2 mM of $MnCl_2$ and cycled for 27 times (pre-incubation at 95° C. for 3 min, then cycling: denaturation at 95° C. for 15 s, annealing at 55° C. for 15 s, extension at 72° C. for 3 min). These conditions typically yielded 1-4 mutations per gene in the final library. The PCR products were pooled together, gel purified (QIAquick Gel Extraction Kit, Qiagen) and cloned into a pT7 expression plasmid (pT7-SC1) by MEGAWHOP procedure: ~500 ng of the purified PCR product was mixed with ~300 ng of pT7-SC1 plasmid containing 10R FraC gene and the amplification was carried out with Phire Hot Start II DNA polymerase (Finnzymes) in 50 μL final volume (pre-incubation at 98° C. for 30 s followed by 30 cycles: denaturation at 98° C. for 5 s, extension at 72° C. for 1.5 min). The circular template was eliminated by incubation with Dpn I (1 FDU) for 2 hr at 37° C. Of the resulting mixture 0.6 μL was transformed into E. cloni® 10G cells (Lucigen) by electroporation. The transformed bacteria were grown overnight at 37° C. on ampicillin (100 μg/ml) LB agar plates typically resulting in >$10^5$ colonies which were harvested for plasmid DNA library preparation.

Screening for Hemolytic Activity in Crude Lysates after FraC Overexpression

Overnight starter cultures from 600 clones (see above) were inoculated into 450 μL of fresh medium in new 96-deep-well plates and cultures were grown at 37° C. until OD600~0.8. Then, IPTG (0.5 mM) was added to induce overexpression and the temperature was reduced to 25° C. for an overnight incubation. Bacteria were harvested the following day by centrifugation at 3000×g for 15 min at 4° C. The supernatant was discarded and pellets were frozen at −80° C. for two hours to facilitate cell disruption. Cell pellets were then resuspended in 0.4 mL of lysis buffer (15 mM Tris.HCl pH 7.5, 1 mM MgCl2, 10 μg/ml lysozyme, 0.2 units/mL DNAse I) and lysed by shaking at 1300 RPM for 30 min at 37° C. Of the crude lysate 0.5-5 μL were then added to 100 μL of ~1% horse erythrocytes suspension. The latter was prepared by centrifuging horse blood (bioMérieux Benelux) at 6000×g for 5 mi at 4° C. and pellet resuspension in 15 mM Tris.HCl pH 7.5, 150 mM NaCl. If the supernatant had a red color, the solution was centrifuged again and the pellet resuspended in the same buffer. The hemolytic activity was monitored by the decrease in OD at 650 nm over time (Multiskan GO Microplate Spectrophotometer, Thermo Scientific).

Screening for Mutations that Compensate for Deleterious Effects of D10R Amino Acid Substitution in FraC D10R amino acid substitution resulted in ~5 fold decrease in hemolytic activity of FraC (FIG. 5). Although D10R FraC still could be oligomerized and reconstituted in planar bilayers made from 1,2-diphytanoyl-sn-glycero-3-phosphocholine (DPhPC) we searched for compensatory mutations that recovered the hemolytic activity of D10R FraC back to the WtFraC level. Maintaining the hemolytic activity of FraC is important for two reasons: firstly, it reflects the ability to assemble into oligomeric pores on targeted lipid bilayers and, therefore, may translate into more efficient preparation of oligomeric nanopores. On the other hand, hemolytic activity offers a convenient way to screen the functionality of variants with arbitrary amino acid sequences changes and thus will facilitate future engineering efforts on the FraC nanopore. In order to identify compensatory mutations, we constructed a random mutagenesis library based on D10R FraC gene, transformed it into Bl21 DE3 *E. coli* and screened individual variants for hemolytic activity against horse erythrocytes in crude lysates after overexpression, using WtFraC as reference. In the first round, we screened 600 variants and selected 12 clones as a template for second round of random mutagenesis combined with hemolytic activity screening. Then, 7 clones with the highest level of hemolytic activity were selected for further characterization. Sequence changes that occurred in the corresponding genes are summarized in Table 3.

TABLE 3

Sequence changes that compensate for deleterious effects of D10R mutation in FraC.

| FraC variant | Amino acid sequence changes relative to WtFraC (residue numbering as in crystal structure PDB ID 4TSY) |
|---|---|
| 1 | D10R, T150I, W112L |
| 2 | I9T, D10R |
| 3 | A2S, D10R, G153D |
| 4 | D10R, A34V, A159E |
| ReFraC | D10R, K159E |
| 5 | D10R, I171T |
| 6 | I9T, D10R, F52Y, K159E |

Purified variants were oligomerized in sphingomyelin: DPhPC (1:1) liposomes and solubilized in 0.6% LDAO. After exchanging the detergent to 0.02% DDM by Ni-NTA chromatography, oligomeric proteins were tested for pore-forming activity in planar lipid bilayers composed of DPhPC. Initially, we identified variants named 3, 4 and ReFraC (Table 3) as the most promising pore-formers. However, nanopores made by variant 3 were heterogeneous (less than 50% yielded octameric pores), while pore-forming activity of variant 4 was decaying within days when stored at 4° C. Oligomeric ReFraC has maintained pore—forming activity for months when stored at 4° C. and formed nanopores nearly as uniform as a WtFraC while being able to capture ssDNA. Therefore, we picked ReFraC for further DNA analysis in this study. Further, we replaced aspartate 10 with asparagine in ReFraC yielding a D10N K159E variant, but could not detect ssDNA entry.

```
WtFraC (protein sequence)
                                              SEQ ID NO: 12
MASADVAGAVIDGAGLGFDVLKTVLEALGNVKRKIAVGIDNESGKTWTAM

NTYFRSGTSDIVLPHKVAHGKALLYNGQKNRGPVATGVVGVIAYSMSDGN

TLAVLFSVPYDYNWYSNWWNVRVYKGQKRADQRMYEELYYHRSPFRGDNG

WHSRGLGYGLKSRGFMNSSGHAILEIHVTKAGSAHHHHHH**

WtFraC (DNA sequence)
                                              SEQ ID NO: 11
ATGGCGAGCGCCGATGTCGCGGGTGCGGTAATCGACGGTGCGGGTCTGGG

CTTTGACGTACTGAAAACCGTGCTGGAGGCCCTGGGCAACGTTAAACGCA

AAATTGCGGTAGGGATTGATAACGAATCGGGCAAGACCTGGACAGCGATG

AATACCTATTTCCGTTCTGGTACGAGTGATATTGTGCTCCCACATAAGGT

GGCGCATGGTAAGGCGCTGCTGTATAACGGTCAAAAAAATCGCGGTCCTG

TCGCGACCGGCGTAGTGGGTGTGATTGCCTATAGTATGTCTGATGGGAAC

ACACTGGCGGTACTGTTCTCCGTGCCGTACGATTATAATTGGTATAGCAA

TTGGTGGAACGTGCGTGTCTACAAAGGCCAGAAGCGTGCCGATCAGCGCA

TGTACGAGGAGCTGTACTATCATCGCTCGCCGTTTCGCGGCGACAACGGT

TGGCATTCCCGGGGCTTAGGTTATGGACTCAAAAGTCGCGGCTTTATGAA

TAGTTCGGGCCACGCAATCCTGGAGATTCACGTTACCAAAGCAGGCTCTG

CGCATCATCACCACCATCACTGATAAGCTT
```

FraC Overexpression and Purification

E. cloni® EXPRESS BL21 (DE3) cells were transformed with the pT7-SC1 plasmid containing the FraC gene. Transformants were selected after overnight growth at 37° C. on LB agar plates supplemented with 100 mg/L ampicillin. The resulting colonies were inoculated into 2xYT medium (Sigma) containing 100 mg/L of ampicillin. The culture was grown at 37° C., with shaking at 200 rpm, until it reached an $OD_{600}$ of ~0.8. The expression of FraC was then induced by the addition of 0.5 mM IPTG and the growth was continued at 25° C. The next day the bacteria were harvested by centrifugation at 6000×g for 25 min and pellets were stored at −80° C. The pellets (derived from 50-100 ml of bacterial culture) containing monomeric FraC were thawed and resuspended in 40 ml of 15 mM Tris.HCl pH 7.5, 1 mM MgCl2 and 0.05 units/mL of DNase I (Fermentas). Then, to initiate cell disruption, bacteria suspension was supplemented with 0.2 mg/ml lysozyme and 2 M urea (to prevent debris formation) and was subjected to vigorous shaking at ambient temperature for 40 min. The remaining bacteria were disrupted by probe sonication. The crude lysates were clarified by centrifugation at 6000×g for 20 min and supernatant mixed with 200 μL (bead volume) of Ni-NTA resin (Qiagen) that was pre-equilibrated with wash buffer (10 mM Imidazole 150 mM NaCl, 15 mM Tris.HCl pH 7.5). After 1 hour of gentle mixing at ambient temperature, the resin was loaded onto a column (Micro Bio Spin, Bio-Rad) and washed with ~5 ml of wash buffer. FraC was eluted with approximately ~0.5 mL of wash buffer containing 300 mM imidazole. Protein concentration was determined by the Bradford assay. FraC monomers were stored at 4° C. until further use.

Hemolytic Activity Assay

Defibrinated horse blood (bioMérieux Benelux) was washed with 150 mM NaCl, 15 mM Tris.HCl pH 7.5 until the supernatant was clear. The erythrocytes were then resuspended with the same buffer to ~1% concentration (OD 650 nm 0.6-0.8). The suspension was then mixed with 200 nM of FraC. Hemolytic activity was measured by monitoring the decrease in OD650 using a MultiskanTM GO Microplate spectrophotometer (Thermoscientific). The rate of hemolysis was determined as one over the time elapsed till 50% decrease in turbidity.

Preparation of Sphingomyelin:DPhPC Liposomes 20 mg of the sphingomyelin (Brain, Porcine, Avanti Polar lipids) and DPhPC (1:1) mixture was dissolved in 4 ml of pentane supplemented with 0.5% ethanol (to help dissolving sphingomyelin) and placed in a round bottom flask. The solvent was evaporated while slowly rotating the flask in order to deposit lipid film on the walls. After deposition of the lipid film, the flask was kept open for 30 min to allow the complete evaporation of the solvent. The lipid film was then resuspended in 150 mM NaCl, 15 mM Tris.HCl pH 7.5 (final concentration of the total lipid 10 mg/ml) using a sonication bath (5-10 minutes at ambient temperature). Obtained liposomes were stored at −20° C.

Oligomerization of FraC

Monomeric FraC was mixed with liposomes (lipid/protein mass ratio 10:1) in 150 mM NaCl, 15 mM Tris.HCl pH 7.5 buffer. The mixture was briefly sonicated (sonication bath) and incubated for 30 min at 37° C. Proteoliposomes were then solubilized with 0.6% LDAO and incubated for 5 min and the mixture was diluted 20-fold with DDM-containing wash buffer (0.02% DDM 150 mM NaCl, 15 mM Tris.HCl pH 7.5) and mixed with ~100 μl (bead volume) of Ni-NTA agarose resin (Qiagen) that was pre-equilibrated with DDM-containing wash buffer. After gentle mixing for 1 hour, the resin was loaded onto a column (Micro Bio Spin, Bio-Rad) and washed with ~2 ml of DDM wash buffer. FraC was eluted from the column with 50 μl of elution buffer (200 mM EDTA, 0.02% DDM, pH 8—alternatively we could use 1M imidazole 0.02% DDM, however, EDTA proved more efficient). Purified FraC oligomers were stored at 4° C.

Alternatively, FraC oligomers can be formed by mixing FraC monomers with liposomes formed by sphingomyelin alone (1 hr at 37° C. and then 4° C. overnight). Next day, 5 mM EDTA and 1% DDM (final) is added to the proteoliposomes and incubated for 15 minutes at room temperature. The solution is then diluted to 1 ml volume containing 5 mM EDTA, 0.05% DDM 15 mM Tris HCl 7.5 150 mM NaCl. The solution is then concentrated to ~100 ul with 100 kDa cutoff ultrafiltration device.

Electrical Recordings in Planar Lipid Bilayers

The applied potential refers to the potential of the trans electrode. FraC nanopores were inserted into lipid bilayers from the cis compartment, which was connected to the ground electrode. The two compartments were separated by a 25 μm thick polytetrafluoroethylene film (Goodfellow Cambridge Limited) containing an orifice of ~100 μm in diameter. The aperture was pretreated with ~5 μl of 10% hexadecane in pentane and a bilayer was formed by the addition of ~10 μL of 1,2-diphytanoyl-sn-glycero-3-phosphocholine (DPhPC) in pentane (10 mg/mL) to both electrophysiology chambers. Typically, the addition of 0.01-10 ng of oligomeric FraC to the cis compartment (0.5 mL) was sufficient to obtain a single channel. WtFraC nanopores displayed a higher open pore current at positive than at negative applied potentials, which provided a useful tool to determine the orientation of the pore. Electrical recordings were carried out in 1M (initial characterization of the FraC nanopores) and in 3M NaCl (for polynucleotide analysis to increase amplitudes), 15 mM Tris.HCl pH 7.5.

Data Recording and Analysis

Electrical signals from planar bilayer recordings were amplified using an Axopatch 200B patch clamp amplifier (Axon Instruments) and digitized with a Digidata 1440 A/D converter (Axon Instruments). Data were recorded by using Clampex 10.4 software (Molecular Devices) and the subsequent analysis was carried out with Clampfit software (Molecular Devices). Electrical recordings were acquired by applying a 2 kHz low-pass Bessel filter and a 10 kHz sampling rate. Current transitions from level 0 to level 1 were analyzed with the "single-channel search" function in Clampfit. Residual current values a ($I_{res}$) were calculated from blocked pore current values ($I_B$) and open pore current values ($I_\varphi$) as $I_{res}$=100* $I_B/I_O$. $I_B$ and $I_O$ were determined from Gaussian fits to amplitude histograms of events. In case of events showing stepwise current enhancements, residual current levels were calculated from Gaussian fits to whole point current histograms. To determine event lifetimes, event dwell times ($t_{off}$) were binned together as cumulative distributions and fitted to a single exponential. Frequency of events that show stepwise current enhancements (FIG. 3A) and rotaxane forming blockades were calculated manually. Graphs were made with Origin (OriginLab Corporation) or Clampfit software (Molecular Devices).

Graphic Representation of FraC Nanopore

Molecular graphics was performed with Chimera (http://www.cgl.ucsf.edu/chimera).

Example 1: Reconstitution of Wild Type FraC Pores in Planar Lipid Bilayers

Recombinant wild type FraC (WtFraC, FIG. 1A; 1B, top) protein monomers, genetically fused to a Hi9 tag at the C-terminus, were expressed in a BL21(DE3) *E. coli* strain. Previous works established that pore assembly of actinoporins is triggered by the presence of SM in lipid bilayers.[9],

[10],[11],[8] In agreement, water-soluble monomers of WtFraC purified by Ni-NTA chromatography did not form pores in DPhPC planar lipid bilayers. Therefore, we pre-oligomerized monomers with DPhPC:SM (1:1) liposomes. After solubilization of the liposomes in 0.6% N,N-Dimethyldodecylamine N-oxide (LDAO), to prevent the dissociation of the oligomers,[12] LDAO was exchanged to 0.02% β-Dodecyl maltoside (DDM) by a second round of Ni-NTA chromatography (SI). The addition of purified sub-microgram quantities of oligomeric WtFraC in 0.02% DDM to the cis side of the DPhPC planar lipid bilayer yielded pores readily. Distribution of unitary channel conductance for WtFraC pores at 1 M NaCl, 15 mM Tris.HCl pH 7.5 buffer revealed chiefly a single conductance type (FIGS. 1C; 4A, top), presumably corresponding to the octamer observed in the recently determined crystal structure. [8] Similar to other biological nanopores, WtFraC channels showed asymmetric current-voltage (I-V) relationship (FIG. 4B) allowing the determination of orientation of the pore. An example trace, obtained in 3 M NaCl, 15 mM Tris.HCl pH 7.5 buffer, is shown in FIG. 1D, top.

Example 2: Engineering of WtFraC for Nucleic Acid Analysis

The crystal structure of octameric WtFraC suggests that this nanopore is large enough to allow the threading of ssDNA (1.2 nm constriction diameter). [8] However, in our initial experiments we could not observe ssDNA blockades, most likely because of the negatively charged constriction region of the WtFraC pore prevented DNA translocation. [13],[14] To induce the threading of ssDNA through FraC, we substituted aspartate 10 with arginine, producing a nanopore with a positively charged constriction (FIG. 1B, bottom). Because D10R FraC showed a low pore-forming activity (FIG. 5), we performed random mutagenesis on the background of the D10R FraC gene and screened hemolytic activity of obtained variants (SI). As a result, we identified the compensatory mutation lysine 159 to glutamic acid (K159E) which is located on the outer rim of the wide vestibule (FIG. 1A). The double mutant D10R, K159E of FraC (ReFraC) displayed near wild type-levels of hemolytic activity (FIG. 5) and yielded uniform pores (FIG. 1C), albeit with altered I-V relationship compared to WtFraC (FIG. 4B and FIG. 1D, bottom). The lower conductance of ReFraC pores at ±50 mV in 1 M NaCl, 15 mM Tris.HCl pH 7.5 can be attributed to a narrower constriction as arginine has bulkier side chain than aspartate (FIG. 1B).

Example 3: Polynucleotide Discrimination with ReFraC

We followed established approaches with αHL[7],[15],[16],[17] and MspA[14],[18] to immobilize DNA with neutravidin (NA). We complexed 5'-end biotinylated A20/C20/T20 ssDNA homopolymers with tetrameric NA to assess the ability of ReFraC to translocate and discriminate DNA strands. We added pre-mixed DNA (1 μM)

and NA (0.25 μM) to the cis compartment of the planar lipid bilayer setup and performed DNA discrimination experiments in 3 M NaCl, 15 mM Tris.HCl, pH 7.5 buffer and +70 mV applied potential (referring to the trans electrode). We observed permanent current blockades, which are provoked by pseudorotaxanes where ssDNA is stably threaded through the pore until the applied potential is reversed (FIGS. 2A, 9A). The residual currents, Ires, which are the percentage ratios of the amplitudes of blocked and open pore currents multiplied by 100 ((IB/IO)×100) were: 13.1±0.4% for NA:A20 (N=5, n=364, where N is a number of independent single pore experiments and n the analyzed blockades), 10.8±0.3% (N=4, n=920) for NA:C20 and 14.0±0.3% (N=5, n=780) for NA:T20 (FIG. 2B). To exclude effects of pore-to-pore variation, we also resolved mixtures of homopolymers (FIG. 2C-F). The relatively low residual currents suggest a tight closure of the pore around threaded ssDNA.

Example 4: DNA Unzipping and Double Strand DNA Translocation by ReFraC Nanopores The constriction of ReFraC (1.2 nm) is smaller than the B-form of double stranded DNA (dsDNA, ~2 nm). Thus, in order to evaluate dsDNA as a stopper for DNA analysis, we designed two oligonucleotides: oligo I with a biotin group attached at the 5'-terminus with the sequence bio-5'-A20-GTGCTACGACTCTCTGTGTG-C20-3' SEQ ID NO:1 and a short oligo II with reverse complement sequence to the underlined part of oligo I. Annealing yielded an A(dsDNA)C substrate: a 20 base pair long central segment of dsDNA, flanked by A20 and C20 ssDNA segments. Addition of 1 μl of A(dsDNA)C to the cis compartment at +50 mV caused transient blockades to the ReFraC pore (blockade lifetime 2±5 s, Ires=10.0±0.2%, N=3, n=290, FIG. 6A, left). Increasing the applied potential to +70 mV shortened the blockades lifetime to 2.9±0.4 ms (note that the residual currents showed two current levels: 12.8±0.6% and 3.5±0.5% N=3 n=2700 FIG. 6B, left). The decrease of blockade lifetime. with the potential suggests the translocation of A(dsDNA)C through ReFraC. To prove DNA translocation, we added NA to the cis chamber. NA:A(dsDNA)C blockades became permanent both at |+50 mV, (FIG. 6A, right) and at +70 mV (FIG. 6B, right), therefore suggesting the transient blockades in the absence of NA could not be provoked by the retraction of A(dsDNA)C to the cis compartment. Curiously, at +50 mV, 31±4% of the NA:A(dsDNA)C blockades (N=3, n=468) showed a stepwise enhancement of the residual current from a transient level (FIG. 3A, state "2", Ires=8.8±0.7%) to a stable level (FIG. 3A, state "3", with Ires=12.5±0.7%, N=4, n=46; more examples in FIG. 7). The current level of state "2" was slightly lower than that of NA:C20 (Ires=10.5±0.7; N=3, n=206 at +50 mV). The current level of state "3" matched that of NA:A20. A likely explanation for above current enhancements is that at +50 mV the C20 segment of NA:A(dsDNA)C is dwelling in the constriction of the nanopore (FIG. 3A, state "2"), with the duplex segment preventing the further translocation. However, after the unzipping of the duplex, A20 occupies the constriction of ReFraC, with NA arresting the translocation (FIG. 3A, state "3"). In agreement, at +50 mV, NA:A(dsDNA)C blockades were immediately relieved when the potential was reversed to −30 mV, indicating that at +50 mV translocation of A(dsDNA)C is mediated by unzipping (FIG. 3A, brackets).

In contrast, at +70 mV, a significant fraction of blockades was not immediately released at −30 mV (FIG. 3B, inset), indicating the formation of an interlocked state (FIG. 3B, states "2" and "3"). Further, these interlocked states were generated more frequently with increasing the potential (e.g. from 7±4% of all blockades at +70 mV to 54±14% at +100 mV, N=3, n=739; FIG. 3B, insert). Considering that blockades of oligo I alone in complex with NA were released immediately at −30 mV (FIG. 9A), we attribute such interlocked state to a rotaxane where NA and the duplex DNA segment of A(dsDNA)C serve as cis and trans stoppers, respectively (FIG. 3B, right). Expectedly, such rotaxanes could also be formed from NA:oligo I cis blockades by adding oligo II in trans (FIG. 9B). Switching potential to −40 mV dismantled rotaxanes quickly, presumably via unzipping of the dsDNA stopper in trans (FIGS. 8 and 9B). Formation of a rotaxane from NA:A(dsDNA)C present in cis requires the deformation of the ReFraC pore in order to allow the translocation of the duplex segment of the A(dsDNA)C substrate (FIG. 3B, brackets).

This structural flexibility may be a general feature of α-helical pores. Previously, we observed that the blockades of human thrombin (~4.2 nm diameter) to type I ClyA-CS nanopores (~3.3 nm constriction diameter) were followed by a transient increase in the open pore current.[19] This phenomenon was interpreted as translocation of the protein via the deformed constriction of ClyA.

References to Section A

[1] J. J. Kasianowicz, E. Brandin, D. Branton, D. W. Deamer, *Proc Natl Acad Sci USA* 1996, 93, 13770-13773.
[2] M. Akeson, D. Branton, J. J. Kasianowicz, E. Brandin, D. W. Deamer, *Biophys J* 1999, 77, 3227-3233.
[3] D. Wendell, P. Jing, J. Geng, V. Subramaniam, T. J. Lee, C. Montemagno, P. Guo, *Nature nanotechnology* 2009, 4, 765-772.
[4] L. Franceschini, M. Soskine, A. Biesemans, G. Maglia, *Nature communications* 2013, 4, 2415.
[5] C. Cao, Y. L. Ying, Z. L. Hu, D. F. Liao, H. Tian, Y. T. Long, *Nature nanotechnology* 2016.
[6] A. H. Laszlo, I. M. Derrington, B. C. Ross, H. Brinkerhoff, A. Adey, I. C. Nova, J. M. Craig, K. W. Langford, J. M. Samson, R. Daza, K. Doering, J. Shendure, J. H. Gundlach, *Nat Biotechnol* 2014, 32, 829-833.
[7] D. Stoddart, A. J. Heron, E. Mikhailova, G. Maglia, H. Bayley, *Proc Natl Acad Sci USA* 2009, 106, 7702-7707.
[8] K. Tanaka, J. M. Caaveiro, K. Morante, J. M. Gonzalez-Manas, K. Tsumoto, *Nature communications* 2015, 6, 6337.
[9] A. Barlic, I. Gutierrez-Aguirre, J. M. Caaveiro, A. Cruz, M. B. Ruiz-Arguello, J. Perez-Gil, J. M. Gonzalez-Manas, *J Biol Chem* 2004, 279, 34209-34216.
[10] B. Bakrac, I. Gutierrez-Aguirre, Z. Podlesek, A. F. Sonnen, R. J. Gilbert, P. Macek, J. H. Lakey, G. Anderluh, *J Biol Chem* 2008, 283, 18665-18677.
[11] P. Schon, A. J. Garcia-Saez, P. Malovrh, K. Bacia, G. Anderluh, P. Schwille, *Biophys J* 2008, 95, 691-698.
[12] K. Tanaka, J. M. Caaveiro, K. Tsumoto, Biochemistry 2015, 54, 6863-6866.
[13] G. Maglia, M. R. Restrepo, E. Mikhailova, H. Bayley, *Proc Natl Acad Sci USA* 2008, 105, 19720-19725.
[14] T. Z. Butler, M. Pavlenok, I. M. Derrington, M. Niederweis, J. H. Gundlach, *Proc Natl Acad Sci USA* 2008, 105, 20647-20652.
[15] R. F. Purnell, J. J. Schmidt, *ACS Nano* 2009, 3, 2533-2538.
[16] D. Stoddart, A. J. Heron, J. Klingelhoefer, E. Mikhailova, G. Maglia, H. Bayley, *Nano Lett* 2010, 10, 3633-3637.
[17] D. Stoddart, G. Maglia, E. Mikhailova, A. J. Heron, H. Bayley, *Angew Chem Int Ed Engl* 2010, 49, 556-559.
[18] E. A. Manrao, I. M. Derrington, M. Pavlenok, M. Niederweis, J. H. Gundlach, *PLoS One* 2011, 6, e25723.
[19] M. Soskine, A. Biesemans, M. De Maeyer, G. Maglia, *J Am Chem Soc* 2013, 135, 13456-13463.
[20] J. Mathe, H. Visram, V. Viasnoff, Y. Rabin, A. Meller, *Biophys J* 2004, 87, 3205-3212.
[21] N. An, A. M. Fleming, E. G. Middleton, C. J. Burrows, *Proc Natl Acad Sci USA* 2014, 111, 14325-14331.
[22] M. Faller, M. Niederweis, G. E. Schulz, *Science* 2004, 303, 1189-1192.

Section B

Section A herein above shows that an α-helical pore-forming toxin from an actinoporin protein family Fragaceatoxin C (FraC) is advantageously used for polynucleotide analysis.

Section B demonstrates that FraC nanopores are also suitable to recognize proteins, e.g. biomarkers, in the form of oligopeptides (~10 or fewer amino acids), polypeptides (>10 amino acids) and folded proteins (>50 amino acids).

Materials

Chymotrypsin(from bovine pancreas, ≥85%, C4129), β2-microglobulin(from human urine, ≥98%, M4890), endothelin 1(≥97%, E7764), endothelin 2(≥97%, E9012), angiotensinI(≥90%, A9650), pentane(≥99%, 236705) and hexadecane(99%, 116703), Trizma® hydrochloride (Lot #SLBG8541V) and Trizma® base(Lot #SLBK4455V), N,N-Dimethyldodecylamine N-oxide (LADO, ≥99%, 40234) and n-Dodecyl @-D-maltoside (DDM, ≥98%, D4641) were obtained from Sigma-Aldrich. Human EGF (≥98%, CYT-217) was obtained from PROSPEC. 1,2-diphytanoyl-sn-glycero-3-phosphocholine(DPhPC, 850356P) and sphingomyelin (Brain, Porcine, 860062) were purchased from Avanti Polar lipids. Potassium chloride (≥99%, Lot #BCBL9989V) was bought from Fluka. Citric acid(≥99%, Lot #A0365028) was obtained from ACROS. All polypeptide biomarkers and chemicals were used directly without further purification.

Note: 15 mM Tris, pH 7.5 buffer below used was prepared with the formula from Trizma® protocol: 1.902 g Trizma® HCl and 0.354 g Trizma® Base dissolved in 1 liter $H_2O$ to be 15 mM Tris, pH 7.5.

Methods

Frac Monomer Expression And Purification

A gene encoding FraC with a C-terminal His6 tag was cloned into a pT7-SC1 expression plasmid[1] using NcoI and HindIII restriction digestion sites. For expression, the plasmid was transferred into E. cloni® EXPRESS BL21(DE3) competent cell by electroporation. Transformants were harvested from the LB agar plate containing 100 mg/l ampicillin after overnight incubation at 37° C., and inoculated into 200 ml fresh liquid 2-YT media with 100 mg/l ampicillin. The cell culture was grown at 37° C., with 220 rpm shaking to an optical density at 600 nm of 0.8, then 0.5 mM IPTG was added to the cell culture. The temperature was lowered to 25° C. to induce the expression of FraC protein for 12 hours. Cells were recovered by 4,000 RPM centrifugation for 30 minutes at 4° C. and the cell pellets were kept at −80° C. 50-100 ml of cell culture pellet was thawed at room temperature, resuspended with 30 ml lysis buffer (15 mM Tris pH 7.5, 1 mM $MgCl_2$, 4 M Urea, 0.2 mg/ml lysozyme and 0.05 units/ml DNase) and mixed vigorously with a vertex shaker for 1 hour. In order to fully disrupt the cells, the suspension was sonicated for 2 minutes (duty cycle 10%, output control 3 of a Branson Sonifier 450). The crude lysate was then centrifuged at 6,500 RPM, 20 minutes at 4° C. The supernatant (containing FraC monomers) was transferred to a 50 ml falcon tube containing a 100 μl of Ni-NTA resin (Qiagen, stored at 4° C., and suspended before pipetting out 100 μl), which was pre-washed with 3 ml of washing buffer (10 mM imidazole, 150 mM NaCl, 15 mM Tris, pH 7.5), and incubated at room temperature for 1 hour with gentle mixing. The resin was spun down at 4,000 RPM for 5 minutes at 4° C. Most of the supernatant was discarded and the pellet containing the Ni-NTA resin within ~5 ml of buffer was transferred to a Micro Bio Spin column (Bio-Rad) at RT. The Ni-NTA beads were washed with 10 ml wash buffer and the protein was eluded with 500 μl of 300 mM imidazole. Protein concentration was determined with NanoDrop 2000 (Thermo Scientific). The monomers were stored at 4° C.

Preparation of Sphingomyelin-DPhPC Liposomes 20 mg sphingomyelin (Brain, Porcine, Avanti Polar lipids) was mixed with 20 mg of 1,2-diphytanoyl-sn-glycero-3-phosphocholine (DPhPC, Avanti Polar lipids) and dissolved in 4 ml pentane (Sigma) containing 0.5% v/v ethanol. This lipid mixture was placed to a round flask and rotated slowly near a hair dryer to disperse the lipid well around the wall to evaporate the solvent. The flask was kept open at room temperature for another 30 minutes to let the solvent to evaporate completely. Then 4 ml of buffer (150 mM NaCl, 15 mM Tris, pH 7.5) was added to the dried lipids and the flask was added to a sonication bath for 5 minutes. Liposomes solution was kept at −20° C.

Oligomerization of FraC

Frozen liposomes were sonicated after thawing and mixed with monomeric FraC in a mass ratio 1:1. The FraC and liposome mixture was sonicated in a water bath for ~30 seconds and then kept at 37° C. for 30 minutes. The proteo-liposome was solubilized with 0.6% LADO(N,N-Dimethyldodecylamine N-oxide, 5% w/v stock solution in water), then transferred to a 50 ml falcon tube and diluted 20 times with buffer (150 mM NaCl, 15 mM Tris, pH 7.5, 0.02% DDM). 100 μl of pre-washed Ni-NTA resin (Qiagen) was added to the diluted protein/liposome mixture. After incubation with gentle shaking for 1 hour, the beads were loaded to column (Micro Bio Spin, Bio-Rad) and washed with 10 ml buffer (150 mM NaCl, 15 mM Tris, pH 7.5). FraC oligomers were eluted with 300 μl elution buffer (200 mM EDTA, 75 mM NaCl, 7.5 mM Tris, pH 8, 0.02% DDM). Oligomers can be stable for several weeks at 4° C.

Electrical Recording in Planar Lipid Bilayers

Electrical recordings were performed as described earlier[2]. In short, two chambers were separated by a 25 μm polytetrafluoroethylene film (Goodfellow Cambridge Limited) containing an aperture with diameter of around 100 μm. Two silver/silver-chloride electrodes were submerged into each compartment of the electrophysiology chamber, which was filled with 0.5 ml of buffer. The ground electrode was connected to the cis compartment, the working electrode to trans side. To form a lipid bilayer, ~5 μl of hexadecane solution (10% v/v hexadecane in pentane) was added to the polytetrafluoroethylene film. After ~2 minutes, 10 μl of a 10 mg/ml solution of 1,2-diphytanoyl-sn-glycero-3-phosphocholine (DPhPC) in pentane was added directly to the buffer in both compartments. A lipid bilayer then spontaneously formed by lowering the buffer above and below the aperture in the Teflon film. FraC oligomers were added to the cis side. Under an applied potential, the ionic current of FraC is asymmetric, which helps assessing the orientation of FraC nanopores in the lipid bilayer. FraC nanopores showed the orientation as shown in FIG. 10 when a higher conductance was measured at negative applied potential. Analytes were then added to cis chamber. Two kinds of buffer solutions were used for electrophysiology recording in this study depending on the pH. At pH 7.5 recordings were performed using 1M KCl and 15 mM Tris. When the pH was varied from 7.5 to 4.5, the buffer used contained 1 M KCl, 0.1 M citric acid, and 180 mM Tris.Base. FraC and ReFraC oligomers could insert into lipid bilayer from pH 4.5 to 7.5.

Data Recording and Analysis

Planar bilayer recordings were collected using a patch clamp amplifier (Axopatch 200B, Axon Instruments) and the data digitized with a Digidata 1440 A/D converter (Axon Instruments). Data were acquired by using Clampex 10.4 software (Molecular Devices) and the subsequent analysis was carried out with Clampfit software (Molecular Devices). Events duration (dwell time), time between two events (inter-event time), blocked current levels and open pore levels were detected by "single channel search" function. The current levels of blockades were referred as $I_B$, while the open pore current was referred as $I_o$. Ires %, defined as $(I_B/I_O)*100$, was used to describe the extent of blockade caused by different biomarkers. Average Inter-event times were calculated by binning the inter-event times and applying a single exponential fit to cumulative distributions.

Ion Selectivity Measurement

Ion permeability ratio ($K^+/Cl^-$) was calculated using the Goldman-Hodgking-Katz equation (Equation (1) herein below), which uses the reverse potential ($V_r$) as variable input. The $V_r$ was measured from extrapolation from I-V curves using asymmetric salt concentration condition as follow: Individual FraC nanopores were reconstituted using the same buffer in both chambers (symmetric conditions, 840 mM KCl, 15 mM Tris, pH 7.5, 500 μl) to assess the orientation of the nanopore. 400 μl solution containing 3.36 M KCl, 15 mM Tris, pH 7.5 was slowly added to cis chamber and 400 μl of a buffered solution containing no KCl (15 mM Tris, pH 7.5) was added to trans solution (trans:cis, 467 mM KCl: 1960 mM KCl). The solutions were mixed and I-V curves collected from −30 mV to 30 mV with 1 mV steps. Experiments at pH 4.5 were carried out using the same method but using 0.1 M citric acid buffered solutions. Initially, 500 μl buffer of 840 mM KCl, 0.1 M citric acid, 180 mM Tris.Base was added into both chamber and a single FraC channel obtained. Then, 400 μl of pH 4.5 solution containing 3.36 M KCl, 0.1 M citric acid, 180 mM Tris.Base was slowly added to cis chamber and 400 μl of a buffered solution containing no KCl (0.1 M citric acid, 180 mM Tris.Base, pH 4.5) was added to trans solution (thus yielding a trans:cis ration of 467 mM KCl: 1960 mM KCl). The solutions were mixed and I-V curves collected from −30 mV to 30 mV with 1 mV steps. The directionality of the ion selectivity was also tested by using high KCl concentration in trans chamber and low KCl concentration in the cis chamber. Ag/AgCl electrodes were surrounded with 2.5% agarose bridges containing 2.5 M NaCl.

Example 5: Polypeptides and Protein Capture with FraC Nanopores

To assess FraC nanopores as a sensor for oligopeptides biomarkers, we initially selected endothelin 1, a 2.5 kD oligopeptide of 21 amino acids and α-II-chymotrypsin (henceforth chymotrypsin), a 25 kD globular protein of 245 amino acids (FIG. 10). Analytes were added to the cis side of wild type FraC (WtFraC) nanopores (FIG. 10A) using 1 M KCl, 15 mM Tris, pH 7.5 solutions and an external potential was applied to the "working" electrode located in the trans compartment. Because WtFraC shows gating above ~+50 mV, but is stable at potentials as high as −300 mV, we applied potentials between those limits. Addition of 1 μM of endothelin 1 to the cis compartment did not provoke blockades at ±50 mV (FIG. 10B) and up to −300 mV. Since the constriction of ClyA is lined with asp artic acid residues (FIG. 10A), we reasoned that the protonation of these residues at more acidic conditions should diminish the energy barrier for the translocation of endothelin 1 (carrying a net charge of −2) through the WtFraC constriction. Simultaneously, a less negative endothelin 1 would also migrate more easily towards the trans electrode under negative applied potentials. Endothelin 1 blockades started to be appear at pH 6.4, and their capture frequency increased linearly with decreasing the pH (from 0.6±0.2 events $s^{-1}$ $\mu M^{-1}$ at pH 6.4 to 10.8±2.3 events $s^{-1}$ $\mu M^{-1}$ at pH 4.4). At pH 4.5 (1 M KCl, 0.1 M citric acid, 180 mM Tris.Base), endothelin 1 blockades to WtFraC were observed at −50 mV (Ires %: 9.1±0.1%, dwell time: 5.6±2.0 ms, inter-event time: 5.8±0.7 ms), but not at +50 mV (FIG. 10B).

Encouraged by the effect of a more positive constriction under acidic conditions, we next investigated the capture of endothelin 1 with the D10R, K159E FraC (ReFraC) nanopore, a pore with arginine residues at the constriction engineered in Section A herein above for purposes of DNA analysis. Conversely to WtFraC, ReFraC is stable under positive applied potentials but displays gating at potentials of ~−50 mV. Thus, we only applied voltages between −50 mV to +200 mV to ReFraC. Addition of 1 μM endothelin 1 to the cis compartment elicited blockades at pH 7.5 at +50 mV (dwell time: 3.3±2.2 ms, inter-event time: 1413±223 ms) but not −50 mV (FIG. 10B). Decreasing to pH 4.5 (1 M KCl, 0.1 M citric acid, 180 mM Tris.Base) led to an increase in capture frequency at +50 mV (FIG. 10B, dwell time: 8.5±1.8 ms, inter-event time: 402±79 ms), despite the reduced electrophoretic mobility towards the trans electrode.

Next, the protein chymotrypsin (pI 8.75, Sigma) was tested as an example of a relatively large protein analyte. Protein blockades were observed at −50 mV in pH 7.5 buffer (1 M KCl, 15 mM Tris), although they became homogeneous when we increased the potential to −100 mV (45.2±19.1 events $s^{-1}$ $\mu M^{-1}$, dwell time: 12.0±5.7 ms), while no capture was observed at positive applied potentials (FIG. 10C). Contrary to what was observed with endothelin 1, the capture frequency of chymotrypsin remained constant between pH 7.5 and 5.5 (45.2±19.1 events $s^{-1}$ $\mu M^{-1}$ at pH 7.5, 50.5±22.6 events $s^{-1}$ $\mu M^{-1}$ at pH 6.4, 45.2±20.6 events $s^{-1}$ $\mu M^{-1}$ at pH 5.5), and decreased when the pH was lowered to 4.4 (20.8±5.3 events $s^{-1}$ $\mu M^{-1}$ at pH 4.4). Using ReFraC at pH 7.5, we observed only few blockades at high positive applied potentials (dwell time: 0.2±0.1 ms, inter-event time: 174.3±22.9 ms at +200 mV) but not at −50 mV (FIG. 10C). Decreasing the pH to 4.5 led to an increase in capture frequency (dwell time: 1.3±0.7 ms, 112.5±9.5 events $s^{-1}$ $\mu M^{-1}$, FIG. 9B). Notably, ReFraC showed often shallow gating events at negative applied potentials under acidic conditions as shown in FIG. 10C bottom right. Taken together, both nanopores can capture analytes differing 10-fold in molecular weight (2.5 kD versus 25 kDa).

Example 6: Ion Selectivity and Electrostatic Potential of FraC Nanopores

To gain a better insight into the influence of pH on the electrostatic environment and electro-osmotic flow on the entry of polypeptides inside FraC nanopores, we used the Adaptive Poission-Boltzmann Solver (APBS)(13) and a modified version of the PDB2PQR software(14) to estimate the electrostatic potential inside homology models of WtFraC and ReFraC at pH 7.5 and 4.5 in 1M KCl. The simulations showed that the constriction regions of WtFraC and ReFraC at the center of the nanopore exhibited highly negative and positive potentials, respectively (FIG. 11A). Interestingly, while for WtFraC the lowering of the pH from 7.5 to 4.5 caused a reduction potential at the center of the constriction from −1.2 to −0.7 $k_BT/e_c$ (1 $k_BT/e_c$=25.6 mV at 298 K) respectively, no such effect was observed for ReFraC.

The contribution of the electro-osmotic flow to the capture of analytes with WtFraC and ReFraC pores was estimated by measuring the ion-selectivity of both pores using asymmetric KCl concentrations on either side of the nanopore (1960 mM and 467 mM). The reversal potential ($V_r$), i.e. the potential at which the current is zero (FIG. 11B), was then used, together with the Goldman-Hodgking-Katz equation, to calculate the ion selectivity ($P_{K+}/P_{Cl-}$) of both nanopores:

$$\frac{P_{K^+}}{P_{Cl^-}} = \frac{[a_{Cl^-}]_{trans} - [a_{Cl^-}]_{cis} \cdot e^{V_rF/RT}}{[a_{K^+}]_{trans} \cdot e^{V_rF/RT} - [a_{K^+}]_{cis}} \quad (1)$$

where $[a_x]_{comp}$ is the activity of ion X in the cis/trans compartments, R the gas constant, T the temperature and F the Faraday constant. We found that the ion selectivity of FraC nanopores is dominated by the charge at the constriction, with WtFrac being strongly cation-selective ($P_{K+}/P_{Cl-}$=3.55±0.30, pH 7.5) and ReFraC anion-selective ($P_{K+}/P_{Cl-}$=0.57±0.04, pH 7.5). Lowering of the pH to 4.5 decreased the cation-selectivity of WtFraC ($P_{K+}/P_{Cl-}$=2.02±0.15, pH 7.5) while it increased the anion-selectivity of ReFraC ($P_{K+}/P_{Cl-}$=0.36±0.08, pH 4.5, FIG. 11B).

Example 7: Biomarker Detection with the WtFraC Nanopore

After assessing the capture of chymotrypsin (25 kD, 245 amino acids) and endothelin 1 (12.5 kD, 21 amino acids), which are protein biomarkers for pancreatic cysts (15) and bronchiolitis obliterans (16), respectively, the WtFraC nanopores were used to detect a larger range of protein biomarkers including β2-microglobulin, a 11.6 kDa (99 amino acids) biomarker for peripheral arterial disease (17), human EGF, a 6.2 kDa (53 amino acids) biomarker for chronic kidney disease (18), and angiotensin I, a 1.3 kD (10 amino acids) biomarker for hypertensive crisis (19).

All biomarkers were assessed under negative applied potentials and, with the exception of chymotrypsin, at pH 4.5. The capture frequency of all biomarkers increased with the applied potential. All other parameter tested showed a non-uniform voltage dependency. The residence time of the biomarkers inside WtFraC increased (chymotrypsin), decreased (β2-microglobulin and angiotensin 1) or showed a bi-phasic behavior with the applied potential (EGF and endothelin 1) See FIG. 12. The voltage dependence of the residual current percentage (Ires %) of chymotrypsin decreased with the potential, the Ires % of endothelin 1 increased with the potential, while the Ires % of @2-microglobulin, EGF and angiotensin 1 remained constant. Despite the complex voltage dependency of the current blockades, our results showed that the WtFraC nanopore is capable of distinguishing differently sized oligopeptide and protein biomarkers by virtue of the Ires % of their current blockades alone (FIG. 12).

Example 8: Near-Isoform Oligopeptide Discrimination

In order to challenge our experimental system, we sought to identify highly similar analytes. We chose endothelin 1 (ET-1) and endothelin 2 (ET-2), near-isomeric oligopeptides differing in only one out of twenty-one amino acids (FIGS. 13A and 13B). At −50 mV, we observed distinguishable blockades with unique Ires % and dwell time (FIG. 12B) for ET-1 (Ires % 8.9±0.1%, dwell time 5.6±2.0 ms, N=3, n=600) and ET-2 (6.1±1.4%, dwell time 19.0±5.3 ms, N=3, n=384). This enabled already their identification on an individual blockade level (FIG. 13C).

Surprisingly, when we consecutively added first 2 μM ET-1 (FIG. 13D) followed by 8 μM ET-2 to the same pore (FIG. 13E), we could also separate a mixture of both two distinct populations by plotting the standard deviation of the amplitude of events over their corresponding Ires %. This observation indicates that highly similar (oligo)peptides or other analytes can be discriminated with a FraC nanopore.

The invention claimed is:

1. A system comprising a funnel-shaped proteinaceous nanopore comprising an α-helical pore-forming toxin of an actinoporin protein family, wherein the α-helical pore-forming toxin comprises a mutant Fragaceatoxin C (FraC), wherein the mutant FraC comprises a mutation at a constriction portion of the funnel-shaped proteinaceous nanopore, wherein the mutation comprises an amino acid that faces a lumen of the funnel-shaped proteinaceous nanopore.

2. The system of claim 1, wherein the mutant FraC further comprises one or more compensatory mutation(s) to recover a hemolytic activity of FraC.

3. The system of claim 2, wherein the mutant FraC comprises mutations Asp10Arg and Lys159Glu.

4. The system of claim 1, wherein the mutant FraC comprises one or more additional mutation(s).

5. The system of claim 1, wherein the system is configured to detect a property of a biopolymer by subjecting the funnel-shaped proteinaceous nanopore to an electric field such that the biopolymer interacts with the funnel-shaped proteinaceous nanopore.

6. The system of claim 5, wherein the biopolymer is a protein having a size from 1 kilodalton kDa to 40 kDa.

7. The system of claim 5, wherein the biopolymer is an oligopeptide comprising at most 10 amino acids.

8. The system of claim 5, wherein the biopolymer is a polypeptide comprising at least 10 amino acids.

9. The system of claim 1, wherein the system is configured to detect a property of a biopolymer by subjecting the funnel-shaped proteinaceous nanopore to an electric field such that the biopolymer electrophoretically or electroosmotically translocates through the funnel-shaped proteinaceous nanopore.

10. The system of claim 9, wherein the property is an electrical, chemical, or physical property of the biopolymer.

11. The system of claim 1, wherein the mutation comprises a substitution of a negatively charged amino acid residue into a neutral or positively charged amino acid residue.

12. The system of claim 1, wherein the mutation comprises a substitution of a neutral amino acid residue into a positively charged amino acid residue.

13. The system of claim 4, wherein the mutant FraC comprises the one or more additional mutation(s) at the constriction portion of the funnel-shaped proteinaceous nanopore.

14. The system of claim 1, wherein the mutant FraC is fused to a protein affinity tag.

15. The system of claim 4, wherein the mutant FraC comprises the one or more additional mutation(s) at a position adjacent to the constriction portion of the funnel-shaped proteinaceous nanopore.

16. A method comprising:

applying an electric field to the system of claim 1, wherein the funnel-shaped proteinaceous nanopore comprising the a-helical pore-forming toxin is positioned between a first conductive liquid medium and a second conductive liquid medium, wherein at least one of the first conductive liquid medium or the second conductive liquid medium comprises an analyte, and detecting the analyte by measuring an ion current as the analyte interacts with the funnel-shaped proteinaceous nanopore to provide a current pattern, wherein an appearance of a blockade in the current pattern indicates a presence of the analyte.

17. The method of claim 16, wherein the analyte is a nucleotide, a nucleic acid, an amino acid, a peptide, an oligopeptide, a protein, a polymer, a drug, an ion, a pollutant, a nanoscopic object, or a biological warfare agent.

* * * * *